US008112155B2

United States Patent
Einav et al.

(10) Patent No.: US 8,112,155 B2
(45) Date of Patent: Feb. 7, 2012

(54) NEUROMUSCULAR STIMULATION

(75) Inventors: Omer Einav, Emek Hefer (IL); Ernesto Korenman, RaAnana (IL)

(73) Assignee: Motorika Limited, Hamilton (BM)

( * ) Notice: Subject to any disclaimer, the term of this patent is extended or adjusted under 35 U.S.C. 154(b) by 941 days.

(21) Appl. No.: 11/568,463

(22) PCT Filed: Apr. 28, 2005

(86) PCT No.: PCT/IL2005/000442
§ 371 (c)(1),
(2), (4) Date: Aug. 20, 2007

(87) PCT Pub. No.: WO2005/105203
PCT Pub. Date: Nov. 10, 2005

(65) Prior Publication Data
US 2008/0288020 A1    Nov. 20, 2008

Related U.S. Application Data

(63) Continuation-in-part of application No. 10/597,756, filed as application No. PCT/IL2005/000139 on Feb. 4, 2005, application No. 11/568,463, which is a continuation-in-part of application No. 10/597,602, filed as application No. PCT/IL2005/000135 on Feb. 4, 2005, application No. 11/568,463, which is a continuation-in-part of application No. 10/597,633, filed as application No. PCT/IL2005/000142 on Feb. 4, 2005.

(60) Provisional application No. 60/542,022, filed on Feb. 5, 2004, provisional application No. 60/556,078, filed on Apr. 29, 2004, provisional application No. 60/604,615, filed on Aug. 25, 2004.

(30) Foreign Application Priority Data

| Feb. 4, 2005 | (WO) | PCT/IL2005/000135 |
| Feb. 4, 2005 | (WO) | PCT/IL2005/000139 |
| Feb. 4, 2005 | (WO) | PCT/IL2005/000142 |

(51) Int. Cl.
*A61N 1/04* (2006.01)
(52) U.S. Cl. ........ 607/48; 607/49; 607/50; 607/62; 600/384
(58) Field of Classification Search .......... 607/48, 607/49, 50, 62; 600/384
See application file for complete search history.

(56) References Cited

U.S. PATENT DOCUMENTS

| 3,919,691 A | 11/1975 | Noll |
| 3,929,462 A | 12/1975 | Karmin |
| 4,499,900 A | 2/1985 | Petrofsky et al. |
| 4,582,049 A | 4/1986 | Ylvisaker |
| 4,685,928 A | 8/1987 | Yaeger |

(Continued)

FOREIGN PATENT DOCUMENTS

EP    0304538    3/1989

(Continued)

OTHER PUBLICATIONS

Translation of Notification of Reasons of Rejection Dated Jun. 12, 2009 From the Japanese Patent Office Re.: Application No. 2006-552011.

(Continued)

*Primary Examiner* — Carl H Layno
*Assistant Examiner* — Natasha Patel

(57) ABSTRACT

An apparatus for muscle activation includes least one electrode adapted to deliver a neuromuscular stimulation (NMES) signal to a body portion. A controller provides a NMES signal comprising a sequence of stimulation signals to the electrode. A mechanical motion element coupled to the body portion and a mirror body portion is operatively coupled to the controller. The controller controls the NMES signal in conjunction with the mechanical motion element.

30 Claims, 7 Drawing Sheets

U.S. PATENT DOCUMENTS

| | | | |
|---|---|---|---|
| 4,724,842 A | 2/1988 | Charters et al. | |
| 4,773,398 A | 9/1988 | Tatom | |
| 4,824,104 A | 4/1989 | Bloch | |
| 4,921,244 A | 5/1990 | Berroth | |
| 4,936,299 A | 6/1990 | Erlandson | |
| 5,048,826 A | 9/1991 | Ryan | |
| 5,070,873 A | 12/1991 | Graupe et al. | |
| 5,193,539 A | 3/1993 | Schulman et al. | |
| 5,193,540 A | 3/1993 | Schulman et al. | |
| 5,201,772 A | 4/1993 | Maxwell | |
| 5,211,161 A | 5/1993 | Stef | |
| 5,244,441 A | 9/1993 | Dempster et al. | |
| 5,269,318 A | 12/1993 | Nashner | |
| 5,282,460 A | 2/1994 | Boldt | |
| 5,312,439 A | 5/1994 | Loeb | |
| 5,324,316 A | 6/1994 | Schulman et al. | |
| 5,391,128 A | 2/1995 | DeBear | |
| 5,397,865 A | 3/1995 | Park | |
| 5,405,367 A | 4/1995 | Schulman et al. | |
| 5,413,611 A | 5/1995 | Haslam, II et al. | |
| 5,454,774 A | 10/1995 | Davis | |
| 5,466,213 A * | 11/1995 | Hogan et al. | 601/33 |
| 5,476,103 A | 12/1995 | Nahsner | |
| 5,476,428 A | 12/1995 | Potash et al. | |
| 5,616,104 A | 4/1997 | Mulenburg et al. | |
| 5,662,693 A | 9/1997 | Johnson et al. | |
| 5,690,389 A | 11/1997 | Ekman et al. | |
| 5,755,645 A | 5/1998 | Miller et al. | |
| 5,830,160 A | 11/1998 | Reinkensmeyer | |
| 5,836,304 A | 11/1998 | Kellinger et al. | |
| 5,846,086 A | 12/1998 | Bizzi et al. | |
| 5,853,353 A | 12/1998 | Blümel | |
| 5,919,115 A | 7/1999 | Horowitz et al. | |
| 5,954,621 A * | 9/1999 | Joutras et al. | 482/114 |
| 6,004,244 A | 12/1999 | Simonson | |
| 6,035,465 A | 3/2000 | Rogozinski | |
| 6,051,017 A | 4/2000 | Loeb et al. | |
| 6,057,828 A | 5/2000 | Rosenberg et al. | |
| 6,061,004 A | 5/2000 | Rosenberg et al. | |
| 6,064,912 A * | 5/2000 | Kenney | 607/48 |
| 6,246,200 B1 | 6/2001 | Blumenkranz et al. | |
| 6,270,445 B1 | 8/2001 | Dean, Jr. et al. | |
| 6,379,393 B1 | 4/2002 | Mavroidis et al. | |
| 6,478,721 B1 | 11/2002 | Hunter | |
| 6,592,315 B2 | 7/2003 | Osborne, Jr. | |
| 6,613,000 B1 | 9/2003 | Reinkensmeyer et al. | |
| 6,645,126 B1 | 11/2003 | Martin et al. | |
| 6,774,885 B1 | 8/2004 | Even-Zohar | |
| 6,829,510 B2 | 12/2004 | Nathan et al. | |
| 6,839,594 B2 | 1/2005 | Cohen et al. | |
| 7,381,192 B2 | 6/2008 | Brodard et al. | |
| 2002/0064438 A1 | 5/2002 | Osborne, Jr. | |
| 2002/0094913 A1 | 7/2002 | Valentino | |
| 2003/0032524 A1 | 2/2003 | Lamar et al. | |
| 2003/0199370 A1 | 10/2003 | Bucay-Bissu | |
| 2003/0208109 A1 | 11/2003 | David et al. | |
| 2003/0208246 A1 | 11/2003 | Kotlik et al. | |
| 2004/0102723 A1 | 5/2004 | Horst | |
| 2004/0172097 A1 | 9/2004 | Brodard et al. | |
| 2004/0180768 A1 | 9/2004 | Almada | |
| 2004/0245838 A1 | 12/2004 | Chiu | |
| 2005/0261114 A1 | 11/2005 | Heitzman et al. | |
| 2006/0229164 A1 | 10/2006 | Einav | |
| 2006/0277074 A1 | 12/2006 | Einav et al. | |
| 2006/0293617 A1 | 12/2006 | Einav et al. | |
| 2007/0282228 A1 | 12/2007 | Einav et al. | |
| 2007/0299371 A1 | 12/2007 | Einav et al. | |
| 2008/0132383 A1 | 6/2008 | Einav et al. | |
| 2008/0161733 A1 | 7/2008 | Einav et al. | |

FOREIGN PATENT DOCUMENTS

| | | |
|---|---|---|
| EP | 0569489 | 11/1993 |
| EP | 0703752 | 4/1996 |
| EP | 0862930 | 9/1998 |
| EP | 1145682 | 10/2001 |
| GB | 2357848 | 7/2011 |
| JP | 59-160455 | 9/1984 |
| JP | 60-200312 | 10/1985 |
| JP | 61-071984 | 4/1986 |
| JP | 61-217174 | 9/1986 |
| JP | 61-265151 | 11/1986 |
| JP | 01-316815 | 12/1989 |
| JP | 02-102652 | 4/1990 |
| JP | 05-007608 | 1/1993 |
| JP | 05-026209 | 4/1993 |
| JP | 06-505407 | 6/1994 |
| JP | 07-163626 | 6/1995 |
| JP | 08-322189 | 12/1996 |
| JP | 08-511448 | 12/1996 |
| JP | 03-039345 | 4/1997 |
| JP | 09-173499 | 7/1997 |
| JP | 3044600 | 10/1997 |
| JP | 3048540 | 2/1998 |
| JP | 10-207624 | 8/1998 |
| JP | 11-009574 | 1/1999 |
| JP | 11-155836 | 6/1999 |
| JP | 11-253504 | 9/1999 |
| JP | 2000-102523 | 4/2000 |
| JP | 2000-279463 | 10/2000 |
| JP | 3126901 | 11/2000 |
| JP | 2001-204850 | 7/2001 |
| JP | 3081786 | 8/2001 |
| JP | 2001-299842 | 10/2001 |
| JP | 2002-065891 | 3/2002 |
| JP | 2002-126019 | 5/2002 |
| JP | 2002-127058 | 5/2002 |
| JP | 3087629 | 5/2002 |
| JP | 2003-093451 | 4/2003 |
| JP | 2003-164544 | 6/2003 |
| JP | 2003-190235 | 7/2003 |
| JP | 2004-008751 | 1/2004 |
| WO | WO 92/13504 | 8/1992 |
| WO | WO 98/37926 | 9/1998 |
| WO | WO 98/43700 | 10/1998 |
| WO | WO 98/43701 | 10/1998 |
| WO | WO 98/46127 | 10/1998 |
| WO | WO 02/13673 | 2/2002 |
| WO | WO 02/35457 | 5/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074372 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2006/021952 | 3/2006 |
| WO | WO 2006/061834 | 6/2006 |
| WO | WO 2006/082584 | 8/2006 |

OTHER PUBLICATIONS

Translation of Notification of Reasons of Rejection Dated Sep. 14, 2009 From the Japanese Patent Office Re.: Application No. 2006-552014.

Pfurtscheller et al. "Brain Oscillations Control Hand Orthosis in A Tetraplegic", Neuroscience Letters, 292: 211-214, 2000.

Backlife "The Backlife Idea", Product Information, <http://www.backlife.com>, 27 P., 2003.

Bak "The Complex Motion of Standing Still. Hydraulics, Sensors, and Human Modeling Dsta—Unified by Proprietary Software", <http://www.designnews.com/article/CA73202>, 5 P., 2001.

Burgar et al. "Development of Robots for Rehabilitation Therapy: The Palo Alto VA/Stanford Experience", Journal of Rehabilitation Research and Development, 37(6): 663-673, 2000.

Cameron et al. "Micromodular Implants to Provide Electrical Stimulation of Paralyzed Muscles and Limbs", IEEE Transactions on Biomedical Engineering, 44(9): 781-790, 1997. Abstract.

Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h Col., Paragraph 1—r-h Col., Paragraph 1, Figs.3, 5, p. 716, 1-h Col., Figs.

Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Motek "Motek Medical Rehabilitation: Rehabilitation", <http://www.e-motek.com>, 1 P.
Peasgood et al. "EMG-Controlled Dosed Loop Electrical Stimulation Using A Digital Signal Processor", Electronics Letters, 36(22): 1832-1833, 2000. p. 1832, 1-h Col., Paragraph 1, Fig. 1, p. 1833, r-h Col., Paragraph 1.
Richardson et al. "Comparing Smooth Arm Movement With the Two-Thirds Power Law and the Related Segmented-Control Hypothesis", The Journal of Neuroscience, 22(18): 8201-8211, 2002.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
International Preliminary Report on Patentability Dated Apr. 21, 2010 From the International Preliminary Examining Authority Re.: Application No. PCT/IL05/00138.
Official Action Dated Jul. 7, 2010 From the US Patent and Trademark Office Re.: U.S. Appl. No. 10/597,675.
Translation of Notification of Reason for Rejection Dated Jul. 9, 2010 From the Japanese Patent Office Re. Application No. 2006-552014.
Translation of Decision of Rejection Dated Feb. 1, 2011 From the Japanese Patent Office Re. Application No. 2006-552013.
Translation of Notification of Reason for Rejection Dated Feb. 3, 2011 From the Japanese Patent Office Re. Application No. 2006-552009.
Translation of Notification of Reasons for Rejection Dated Jan. 27, 2011 From the Japanese Patent Office Re. Application No. 2007-510233.
International Preliminary Report on Patentability Dated May 11, 2006 From the International Preliminary Examining Authority Re.: Application No. PCT/IL2005/000137.
International Preliminary Report on Patentability Dated Jan. 23, 2006 From the International Preliminary Examining Authority Re.: Application No. PCT/IL2005/000135.
International Search Report and the Written Opinion Dated Sep. 6, 2006 From the International Searching Authority Re.: Application No. PCT/IL05/01318.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
International Search Report Dated Jun. 2, 2005 From the International Searching Authority Re.: Application No. PCT/IL2005/000139.
International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Oct. 17, 2005 From the International Searching Authority Re.: Application No. PCT/IL05/00138.
International Search Report Dated Aug. 24, 2005 From the International Searching Authority Re.: Application No. PCT/IL2005/000442.
International Search Report Dated Nov. 28, 2005 From the International Searching Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From the US Patent and Trademark Office Re.: U.S. Appl. No. 11/389,773.
Official Action Dated May 19, 2008 From the US Patent and Trademark Office Re.: U.S. Appl. No. 11/207,655.
Official Action Dated Jul. 26, 2007 From the US Patent and Trademark Office Re.: U.S. Appl. No. 11/389,773.
Official Action Dated Sep. 30, 2008 From the US Patent and Trademark Office Re.: U.S. Appl. No. 11/207,655.
Supplementary Partial European Search Report Dated Jan. 29, 2008 From the European Patent Office Re.: Application No. 05774725.5.
Written Opinion Dated Jun. 2, 2005 From the International Searching Authority Re.: Application No. PCT/IL2005/000139.
Written Opinion Dated Jun. 3, 2005 From the International Searching Authority Re.: Application No. PCT/IL2005/000135.
Written Opinion Dated Jun. 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the International Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the International Searching Authority Re.: Application No. PCT/IL05/00141.
Russo "An Other Reality", Maariv, p. 14, Oct. 26, 2004. Hebrew Only!
Viviani et al. "Minimum-Jerk, Two-Thirds Power Law, and Isochrony: Converging Approaches to Movement Planning", Journal of Experimental Psychology: Human Perception and Performance, 17: 32-53, 1995. Abstract.
Viviani et al. "Trajectory Determines Movement Dynamics", The Journal of Neuroscience, 7: 431-437, 1982.
Official action dated Sep. 14, 2010 from the US patent and trademark office re. U.S. Appl. No. 10/597,756.
Response dated Sep. 27, 2010 to notification of reasons for rejection of Jul. 12, 2010 from the Japanese patent office re. Application No. 2006-215045.
Response dated Sep. 20, 2010 to notice of reason for rejection of Jun. 4, 2010 from the Japanese patent office re. Application No. 2007-529131.
Response dated Sep. 22, 2010 to notification of reasons of rejection of May 26, 2010 from the Japanese patent office re. Application No. 2006-552013.
Response dated Sep. 26, 2010 to notification of reason for rejection of Jul. 9, 2010 from the Japanese patent office re. Application No. 2006-552014.
Translation of notification of reason for rejection dated Aug. 13, 2010 from the Japanese patent office re. Application No. 2006-552009.
Communication Pursuant to Article 96(2) Dated Dec. 11, 2006 From the European Patent Office Re.: Application No. 05703180.9.
Examination Report Dated Oct. 23, 2008 From the Instituto Mexicano de la Propriedad Industrial Re.: Application No. PA/a/2006/008919.
Examination Report Dated Oct. 29, 2008 From the Instituto Mexicano de la Propriedad industrial Re.: Application No. PA/a2006/008914.
International Preliminary Report on Patentability Dated Aug. 16, 2007 From the International Bureau of WIPO Re.: Application No. PCT/IL2006/000140.
International Preliminary Report on Patentability Dated Jan. 19, 2007 From the International Preliminary Examining Authority Re.: Application No. PCT/IL05/00138.
International Preliminary Report on Patentability Dated Apr. 26, 2007 From the International Bureau of WIPO Re.: Application No. PCT/IL2005/000139.
International Preliminary Report on Patentability Dated Sep. 29, 2008 From the International Preliminary Examining Authority Re.: Application No. PCT/IL06/00140.
International Search Report and the Written Opinion Dated Jan. 3, 2007 From the International Searching Authority Re.: Application No. PCT/IL06/00140.
Office Action Dated Sep. 26, 2008 From the State Intellectual Properety Office of the People's Republic of China Re.: Application No. 20580010391.4.
Official Action Dated Oct. 1, 2008 From the US Patent and Trademark Office Re.: U.S. Appl. No. 11/389,773.

Communication of Results From Examination Dated Oct. 23, 2008 From the Instituto Mexicano de la Propriedad Industrial Re.: Application No. PA/a/2006/008914 and its Translation into English.
Communication Pursuant to Article 94(3) EPC Dated Oct. 12, 2009 From the European Patent Office Re.: Application No. 06704564.1.
International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and Its Translation Into English.
Official Action Dated Dec. 18, 2009 From the US Patent and Trademark Office Re.: U.S. Appl. No. 11/348,128.
Official Action Dated Mar. 19, 2010 From the US Patent and Trademark Office Re.: U.S. Appl. No. 10/597,675.
Official Action Dated May 19, 2009 From the US Patent and Trademark Office Re.: U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and Its Translation Into English.
Official Action Dated Jun. 24, 2009 From the US Patent and Trademark Office Re.: U.S. Appl. No. 11/207,655.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Response Dated Apr. 19, 2010 to Official Action of Mar. 19, 2010 From the US Patent and Trademark Office Re.: U.S. Appl. No. 10/597,675.
Supplementary Partial European Search Report and the European Search Opinion Dated Jul. 14, 2009 From the European Patent Office Re.: Application No. 06704564.1.
Translation of Notification of Reasons for Rejection Dated Dec. 15, 2010 From the Japanese Patent Office Re. Application No. 2009-027772.
Response Dated Nov. 1, 2010 to Decision of Rejection of Jul. 9, 2010 From the Japanese Patent Office Re. Application No. 2006-552015.
Response Dated Dec. 6, 2010 to Official Action of Jul. 7, 2010 From the US Patent and Trademark Office Re.: U.S. Appl. No. 10/597,675.
Translation of Decision of Rejection Dated Jul. 9, 2010 From the Japanese Patent Office Re. Application No. 2006-552015.
Translation of Decision of Rejection Dated Oct. 29, 2010 From the Japanese Patent Office Re. Application No. 2007-529131.
Response Dated Aug. 4, 2010 to Notification of Reasons of Rejection of Mar. 9, 2010 From the Japanese Patent Office Re.: Application No. 2006-552008.
Translation of Notification of Reasons for Rejection Dated Jul. 12, 2010 From the Japanese Patent Office Re. Application No. 2006-215045.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Notice of Allowance Dated Feb. 16, 2011 From the US Patent and Trademark Office Re.: U.S. Appl. No. 10/597,675.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009-027772.
Official Action Dated Jun. 15, 2010 From the US Patent and Trademark Office Re. U.S. Appl. No. 10/597,671.
Translation of Notification of Reasons for Rejection Dated Jun. 6, 2011 From the Japanese Patent Office Re. Application No. 2009-027772.
Response Dated Jun. 14, 2011 to Notification of Reason for Rejection of Feb. 3, 2011 From the Japanese Patent Office Re. Application No. 2006-552009.
Translation of Decision of Rejection Dated Jun. 30, 2011 From the Japanese Patent Office Re. Application No. 2007-510233.
Official Action Dated Jul. 18, 2011 From the US Patent and Trademark Office Re. U.S. Appl. No. 10/597,602.
Response Dated Aug. 9, 2011 to Questioning of May 25, 2011 From the Japanese Patent Office Re. Application No. 2006-552015.
Official Action Dated Sep. 1, 2011 From the US Patent and Trademark Office Re.: U.S. Appl. No. 11/660,965.
Official Action Dated May 9, 2011 From the US Patent and Trademark Office Re.: U.S. Appl. No. 11/568,463.
Response Dated May 16, 2011 to Official Action of Mar. 15, 2011 From the US Patent and Trademark Office Re. U.S. Appl. No. 10/597,602.
Translation of Questioning Dated May 25, 2011 From the Japanese Patent Office Re. Application No. 2006-552015.
Translation of Notification of Reasons of Rejection Dated Jul. 4, 2011 From the Japanese Patent Office Re. Application No. 2006-552013.
Response Dated Jul. 6, 2011 to the Notification of Reasons for Rejection of Apr. 6, 2011 From the Japanese Patent Office Re. Application No. 2006-215045.
Response Dated Jun. 9, 2011 to Official Action of May 9, 2011 From the US Patent and Trademark Office Re.: U.S. Appl. No. 11/568,463.
Response Dated Jul. 12, 2011 to Official Action of Jun. 15, 2011 From the US Patent and Trademark Office Re. U.S. Appl. No. 10/597,671.
Examination Report Dated Aug. 25, 2011 From the Government of India, Patent Office Intellectual Property Building Re.: Application No. 3230/CHENP/2006.
Examination Report Dated Aug. 25, 2011 From the Government of India, Patent Office, Intellectual Property Building Re. Application No. 3232/CHENP/2006.
Examination Report Dated Aug. 25, 2011 From the Government of India, Patent Office, Intellectual Property Building Re.: Application No. 3231/CHENP/2006.
Response Dated Aug. 24, 2011 to Notification of Reasons for Rejection of Jun. 6, 2011 From the Japanese Patent Office Re. Application No. 2009-027772.
Official Action Dated Mar. 15, 2011 From the US Patent and Trademark Office Re. U.S. Appl. No. 10/597,602.
Response Dated Feb. 22, 2011 to Decision of Rejection of Oct. 29, 2010 From the Japanese Patent Office Re. Application No. 2007-529131.
Notice of Reasons for Rejection Dated Aug. 31, 2011 From the Japanese Patent Office Re. Application No. 2006-552009 and Its Translation Into English.
Official Action Dated Aug. 10, 2011 From the US Patent and Trademark Office Re. U.S. Appl. No. 10/597,633.
Response Dated Oct. 17, 2011 to Official Action of Jul. 18, 2011 From the U.S. Patent and Trademark Office Re. U.S. Appl. No. 10/597,602.

* cited by examiner

NEUROMUSCULAR STIMULATION

RELATED APPLICATIONS

The present application is a US National Phase of PCT Application No. PCT/IL2005/000442, flied on Apr. 28, 2005 and is a Continuation-In-Part of the following applications: 10/597,756 which is a US national phase of PCT/IL2005/000139 filed on Feb. 4, 2005, 10/597,602 which is a US national phase of PCT/IL2005/000135, filed on Feb. 4, 2005, and 10/597,633 which is a US national phase of PCT/IL2005/000142 filed on Feb. 4, 2005 which claims the benefit under 119(e) of U.S. Provisional Application No. 60/542,022, filed on Feb. 5, 2004, The present application claims benefit under 119(e) of U.S. Provisional Application 60/566,078 filed on Apr. 29, 2004, and U.S. Provisional Application 60/604,615, filed on Aug. 25, 2004. The disclosures of all these applications are incorporated herein by reference. This application is also related to the following PCT applications: PCT/IL2005/000136 filed on Feb. 4, 2005, PCT/IL2005/000138 filed on Feb. 4, 2005, PCT/IL2005/000137 filed on Feb. 4, 2005, PCT/IL2005/000140 filed on Feb. 4, 2005 and PCT/IL2005/000141 filed on Feb. 4, 2005. The disclosures of all these applications are incorporated herein by reference.

FIELD OF THE INVENTION

The field of the invention is devices for rehabilitation of patients with motor control problems.

BACKGROUND OF THE INVENTION

Voluntary muscle movement is caused by electrical impulses which originate in the somato-motor cortex of the brain. A neuron in the somato-motor cortex sends electrical signals to a motor neuron in the spinal cord, which in turn sends electrical signals which stimulate the contraction of muscle fibers, producing movement. All of the muscle fibers which are stimulated by a given motor neuron are called a "motor unit." Each muscle fiber exhibits an electrical potential across its cell membrane, which changes when the muscle contracts.

In electromyography (EMG), the difference in potential on the surface of the skin is measured between the center and the ends of a muscle, which gives a measure of the number of contracting muscle fibers. EMG is regularly used to diagnose a variety of medical conditions in patients, as well as in healthy subjects for research on muscle function.

In stroke patients with damage to their somato-motor cortex, electrical signals are not generated for one or more muscles or parts of muscles, or do not reach those muscles, and normal contraction of those muscles is impossible. Often, residual EMG signals, too weak or too spread out to cause the muscles to contract, are still detectable.

Neuromuscular electrical stimulation (NMES) is used to produce contraction of a muscle which cannot contract normally in a stroke patient. NMES may stop spasticity in a muscle, and may prevent the muscle from atrophying. It is also known to turn NMES of a single muscle on or off in response to residual EMG signals detected from that muscle, thereby allowing the muscle to contract under the control of the patient.

Wireless implantable electronic stimulators have been described, for example in: U.S. Pat. Nos. 5,193,539, 5,193,540, 5,312,439, 5,324,316, 5,405,367, PCT Publication WO 98/37926, PCT WO 98/43700, PCT Publication, WO 98/43701 Oct. 8, 1998, U.S. Pat. No. 6,051,017, U.S. application Ser. No. 09/077,662 and in an article "Micromodular Implants to Provide Electrical Stimulation of Paralyzed Muscles and Limbs", by Cameron, et al., published in IEEE Transactions on Biomedical Engineering, Vol. 44, No. 9, pages 781-790. The disclosures of all of these references are incorporated herein by reference.

The NESS H200 is an external worn stimulator for stimulating muscles in the forearm and hand, for rehabilitation. Some details are provided in U.S. Pat. No. 6,829,510, the disclosure of which is incorporated herein by reference.

SUMMARY OF THE INVENTION

An aspect of some embodiments of the invention relates to the combined use of electrodes for sensing and/or stimulation of EMG and a robotic actuator for moving body limbs. In an exemplary embodiment of the invention, the actuator is used to guide motion in conjunction with the stimulation and/or sensing of activity of one or more muscle groups. Optionally, the guided motion is in the same and/or a different limb from the sensed limb. In some embodiments of the invention, a means other than a robot are used to move and/or sense movement and/or force of a limb.

In an exemplary embodiment of the invention, the actuator is used to calibrate the use of the electrodes. Alternatively or additionally, the actuator is used to train a user and/or controlling device in the use of the electrodes. Optionally, the actuator is used to show a user how various NMES sequences are expected to be translated into movements.

In an exemplary embodiment of the invention, the electrodes are wireless wearable electrodes. Alternatively or additionally, the electrodes comprise implanted electrodes. Optionally, the electrodes are totally implanted.

Optionally, the electrodes are implanted for short term use. Alternatively or additionally, the electrodes are provided as prosthesis, whose use (initial and/or ongoing) is facilitated by the actuator.

In an exemplary embodiment of the invention, the actuator is used to detect the actual effect of the stimulators, optionally including long term changes in the effect.

In an exemplary embodiment of the invention, the actuator is used to support rehabilitation and/or daily activities conducted without the actuator, for example, using recording and playback.

In an exemplary embodiment of the invention, sensing of EMG is used as an indication of the effect of the robotic actuator.

In an exemplary embodiment of the invention, the robotic actuator is used to supplement stimulation and/or serves as an aid to a patient to generate correct EMG.

In an exemplary embodiment of the invention, the electrodes are controlled using a controller. In an exemplary embodiment of the invention, the controller is programmed to control a plurality of electrodes, in a certain sequence and/or power level. In an exemplary embodiment of the invention, when a plurality of electrodes are provided, measurement of actual movement using an actuator robot is used to decide which electrodes to use and/or at what timing and/or at what power level. Optionally, the plurality of electrodes are attached to multiple muscles, one or more electrodes at each muscle. Optionally, the electrodes are attached at different locations along a same muscle. Optionally, the electrodes are provided for multiple joints in the body, optionally for multiple limbs and/or body sides.

An aspect of some embodiments of the invention concerns applying NMES to a paretic arm, or any other part of the body with voluntary muscles, in a manner which is insufficient to cause a desired motion. In an exemplary embodiment of the invention, the desired motion is provided or assisted by an actuator which moves or helps move the paretic portion. Alternatively or additionally, a patient provides the required additional neural signals (e.g., via natural pathways). In some embodiments the actuating device is used to resist motion and/or to guide the motion to a desired pathway. Optionally, a controller is provided storing thereon a plurality of desired motions and expected responses by the patient to various stimulation and assistance levels.

In an exemplary embodiment of the invention, the NMES is provided at an amplitude that would be too low to produce motion by itself, but which, in combination with nerve impulses arising in the patient's motor cortex, allow the arm or other body part to move, or to move more effectively than without the NMES. It does this, for example, by producing muscular feedback which helps to train the motor cortex to move that body part. In some embodiments, the NMES need not be very strong, or very precisely directed, in order to do this. Whenever this application refers to arms, it should be understood that any other body part, or combination of body parts, with voluntary muscles may be used instead. Optionally, EMG signals from the same arm, or from the corresponding muscles in the patient's other arm, or from the arm of another person, are used to determine the pattern (e.g., timing and/or amplitude) of the NMES.

An aspect of some embodiments of the invention concerns the use of EMG signals from one arm, optionally a healthy arm, undergoing voluntary motion, to determine a pattern of NMES to be applied to another, paretic arm. Optionally EMG signals from the paretic arm are also used, at least to determine the timing of the NMES. Optionally, the healthy arm is the other arm of the patient, and the patient tries to move both arms in synchrony, in a mirror symmetric pattern.

Optionally, for either of these embodiments of the invention, the EMG and NMES involve a coordinated sequence of contractions of more than one muscle, and/or a range of amplitudes for the NMES, rather than having the NMES either on or off for a single muscle.

By providing feedback, through the kinesthetic sense, of a coordinated sequence of muscle contractions, the patient's nervous system may be encouraged to utilize alternative undamaged pathways for nerve impulses, or alternative locations in the motor cortex, and the patient can learn to move his arm more effectively on his own. This may be especially true if the NMES is coordinated with the weak nerve impulses that the patient produces on his own, as measured by the EMG.

Optionally, a device, for example a robotic arm, which monitors and displays the movement of the arm, is used for the paretic arm, and optionally also for the healthy arm, if one is used. Information about the movement of the arm can provide further feedback to the patient, as well as feedback for controlling the NMES, and feedback to a physical therapist who is monitoring the progress of the patient's rehabilitation. A robotic arm or similar device can also mechanically move the paretic arm, complementing the NMES by providing a different kind of kinesthetic feedback. A robotic arm can also exert a force working against the muscle, providing a way to strengthen the arm, as well as to measure progress in strengthening the arm.

There is thus provided in accordance with an exemplary embodiment of the invention, apparatus for muscle activation, comprising:

at least one electrode adapted to deliver a neuromuscular stimulation (NMES) signal to a body portion;

at least one controller adapted to provide a NMES signal comprising a sequence of stimulation signals to said at least one electrode; and a mechanical motion element coupled to at least one of said body portion and a mirror body portion, wherein said mechanical motion element is operatively coupled to said at least one controller and wherein said at least one controller controls said NMES signal in conjunction with said mechanical motion element.

Optionally, said mechanical motion element moves said body portion. Alternatively or additionally, said mechanical motion element measures motion of said body portion, which motion is in response to said NMES sequence.

In an exemplary embodiment of the invention, said mechanical motion element guides motion of said body portion, which motion is in response to said NMES sequence.

In an exemplary embodiment of the invention, said mechanical motion element guides motion of said mirror body portion, which NMES is generated in response to said motion.

In an exemplary embodiment of the invention, the apparatus comprises a programmer adapted to program NMES sequences for said electrodes. Optionally, said programmer includes a sequence optimizer which modifies NMES sequences in response to at least one optimization criterion. Optionally, said optimization criterion comprises the ability of a patient. Alternatively or additionally, said optimization criterion comprises electrode limitations. Alternatively or additionally, said optimization criterion comprises a quality of result, as measured by said mechanical motion element.

In an exemplary embodiment of the invention, the apparatus comprises an EMG sensor, wherein said controller is adapted to generate an NMES sequence based on sensed EMG signals from said sensor. Optionally, said EMG signals are measured from a mirror body portion. Alternatively or additionally, said EMG signals are measured from a different person. Alternatively or additionally, said EMG signals are measured from the same body portion. Optionally, said controller generates a NMES signal responsive to at least one of an amplitude and existence of EMG signal at a location to which NMES is to be applied.

In an exemplary embodiment of the invention, said controller is adapted to generate an indication of which electrodes of said at least one electrode to use.

In an exemplary embodiment of the invention, the apparatus comprises a memory storing therein a plurality of NMES sequences, for at least one daily activity.

In an exemplary embodiment of the invention, the apparatus comprises a user input for generating a NMES sequence.

In an exemplary embodiment of the invention, said controller is adapted to generate a NMES sequence for use for said electrodes based on a desired motion of said body part.

In an exemplary embodiment of the invention, said controller is adapted to modify a stored NMES sequence for use for said electrodes based on a desired motion of said body part.

In an exemplary embodiment of the invention, said controller is adapted to compare an actual effect of a NMES sequence and a desired effect of said sequence and detect at least one deviation.

In an exemplary embodiment of the invention, said mechanical motion element is adapted to measure force applied by said body portion in response to said NMES.

In an exemplary embodiment of the invention, the apparatus comprises a calibrator adapted to calibrate at least one sensor associated with motion of said portion.

In an exemplary embodiment of the invention, the apparatus comprises an interactive user guide for electrode NMES programming.

In an exemplary embodiment of the invention, said electrodes are implantable.

In an exemplary embodiment of the invention, said electrodes form part of a prosthesis.

In an exemplary embodiment of the invention, said electrodes are adapted to be worn for the long term.

In an exemplary embodiment of the invention, said electrodes and at least one of said at least one controller are adapted to act independently of and removed from said motion element.

In an exemplary embodiment of the invention, said NMES sequence comprises a sequence for application to at least two muscles.

In an exemplary embodiment of the invention, said NMES sequence is at least 20 seconds long.

In an exemplary embodiment of the invention, said mechanical motion element comprises an actuator. Optionally, said actuator comprises a robotic actuator with at least 3 degrees of motion.

There is also provide din accordance with an exemplary embodiment of the invention, a method of electrode setting for NMES, comprising:

applying a NMES sequence to a limb;
measuring motion of the limb;
modifying said NMES sequence responsive to said measured motion; and
repeating said applying, said measuring and said modifying, using a mechanical motion element to at least one of move said limb, resist motion of said limb and measure motion of said limb.

BRIEF DESCRIPTION OF THE DRAWINGS

Exemplary embodiments of the invention are described in the following sections with reference to the drawings. The drawings are generally not to scale and the same or similar reference numbers are used for the same or related features on different drawings.

DETAILED DESCRIPTION OF EXEMPLARY EMBODIMENTS

Exemplary Apparatus for Applying NMES

Figure 1:
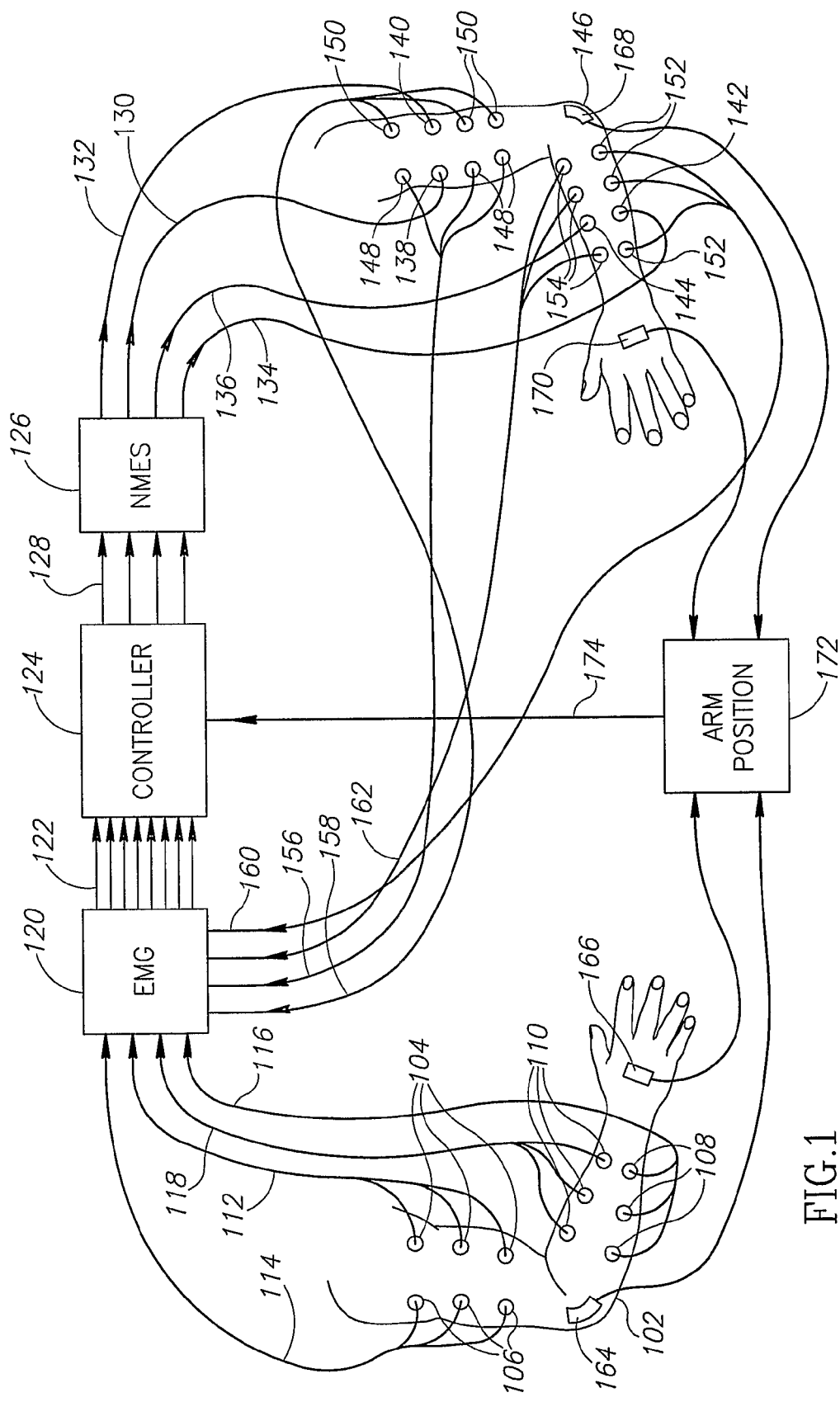
FIG. 1 is a schematic drawing of a healthy arm with EMG electrodes, an EMG unit, a signal processing unit, an NMES unit, and a paretic arm with NMES and EMG electrodes, according to an exemplary embodiment of the invention.

FIG. 1 shows an apparatus for applying NMES to several muscles of a paretic arm, guided by EMG signals from the corresponding muscles of a healthy arm. Healthy arm 102, belonging either to the patient with the paretic arm or to someone else, has EMG electrodes attached to the skin. The person whose arm it is moves the arm voluntarily in a particular pattern, which generates a certain time-dependent pattern of EMG voltages in the muscles. There are optionally four EMG channels, one channel measuring EMG signals from each of four muscles: the biceps, the triceps, the flexors, and the extensors. Each channel uses three electrodes, two recording signals from near each end of the muscle, and one reference electrode in the middle. For example, electrodes 104 measure the biceps, electrodes 106 measure the triceps, electrodes 108 measure the flexors, and electrodes 110 measure the extensors. It should be understood from the description of the present invention that similar arrangements are optionally arranged for other muscle pair groups, such as the pectoralis major and deltoid pairs. When the arm is moved voluntarily, these electrodes transmit the EMG signals corresponding to the pattern of muscle contractions producing that movement of the arm, via cable bundles 112, 114, 116, and 118, to an EMG device 120. The EMG device, or a separate controller, does preliminary processing of the EMG signals, for example amplifying them, digitizing them, and/or recording them. Electrodes may also be provided for multiple joints, such as shoulder, elbow and wrist and optionally multiple limbs, such as arm and leg.

As will be described further below, in some embodiments of the invention, the electrodes are wireless electrodes, for example mounted on or implanted in the limb. Optionally, each electrode has its own controller. Optionally, a memory for recording EMG is provided with each electrode. Optionally, a wireless controller is provided for multiple electrodes. In an alternative embodiment, a portable controller is provided for a plurality of electrodes. Optionally, the controller is wearable and can be used in daily activities of the patient without undue interference therewith.

Figure 2:
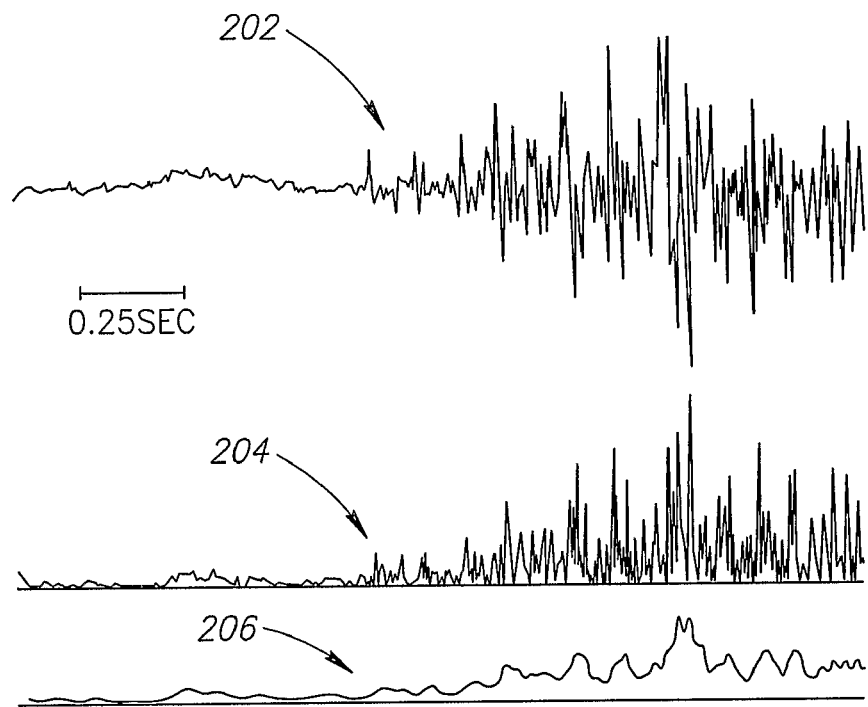
FIG. 2 shows plots of a raw EMG signal, rectified signal, smoothed RMS signal, according to an exemplary embodiment of the invention.

The EMG signals are then transmitted, via a cable 122, to a controller 124, which is, for example, a personal computer, or comprises special dedicated hardware. The controller optionally further processes the EMG signals, for example filtering them, rectifying them, smoothing them, changing the timing, or cutting and pasting parts of a sequence in a different order. The signal processing is optionally done automatically, or is partly or entirely under the control of the physical therapist. FIG. 2 shows a plot of a filtered raw EMG signal 202 from one channel, a rectified signal 204, and a smoothed rectified signal 206, in which the root mean square of the signal is calculated in each of a sequence of time intervals, for example, every 10 milliseconds. The smoothed rectified signal is a measure of the overall degree of contraction of the muscle or section of the muscle measured by that channel, while eliminating high frequency noise associated with the changes in potential of individual muscle fibers. Optionally, the smoothed rectified EMG signal is averaged over many repetitions of the same pattern of movement. Optionally, the EMG sensors add up or average the EMG signals coming from several different sections of the muscle, or this is done by the signal processing. An optional type of signal processing is validating EMG signals, for example, by measuring the actual motion of a healthy limb while measuring EMG thereon, so that it is clear that the EMG signals result from the desired movement. Optionally, one or more of the parameters of the signal processing are controlled by the therapist. In some embodiments of the invention, the smoothed rectified EMG signal is created by dispensing with anomalous EMG readings, such as not factoring the high and low readings, and averaging the rest of the readings over multiple repetitions. In some embodiments, the EMG is measured and the NMES applied, at a time delay, for example, to allow multiple EMG signals to be collected and averaged.

Controller 124 also controls NMES device 126, via cable 128. Optionally, controller 124 commands NMES device to produce NMES signals in each of four channels. The signals in the four channels travel through cables 130, 132, 134, and 136, to electrodes 138, 140, 142, and 144, which respectively stimulate the biceps, triceps, flexors, and extensors on the patient's paretic arm 146 (or optionally any other muscle pair as the case may be). Optionally, the NMES signals in each channel are given a time-dependent amplitude which will produce the same movement in the paretic arm as was performed by the healthy arm. This is done, for example, by making the signal strength in each NMES channel depend on the processed signal amplitude from a corresponding one of the four EMG channels. For example, the NMES signal is proportional to the processed EMG signal amplitude, or is a fixed monotonic function of the processed EMG signal amplitude, for the corresponding channel.

Optionally, the NMES signal depends also on the EMG signal from one or more other channels. For example, because the biceps and triceps work against each other, the NMES signals controlling the biceps and triceps, optionally depend on a linear combination of the EMG signal from the biceps and the EMG signal from the triceps, with a negative coefficient for the EMG signal from the triceps. If the linear combination is positive, only the biceps muscle is stimulated, and if the linear combination is negative, only the triceps muscle is stimulated. A similar method is optionally used for any other pair of agonist-antagonist muscles, such as the flexors and extensors which also work against each other.

Optionally, the NMES signals are based not directly on the EMG signals from the corresponding muscles, but are modified to produce motion that is reversed in some way from the motion associated with the EMG signals. For example, if the EMG signals come from a left arm and the NMES signals are applied to a right arm, then optionally the NMES signals are changed to produce motion in the right arm that is the same as the motion of the left arm, rather than a mirror image of it, as would occur if the corresponding muscles in the two arms were to contract at the same time. Alternatively or additionally, whether or not the two arms are a left arm and a right arm, if the motion of the healthy arm is cyclical, then the NMES signals are changed to produce motion in the paretic arm that is 180 degrees out of phase from the motion of the healthy arm. Such a modification in the NMES signals might be particularly useful to use for the left and right legs, for example, in a patient who needs to relearn how to walk or ride a bike.

Optionally, there are also EMG electrodes 148, 150, 152, and 154, attached to the paretic arm. These sensors send signals along cables 156, 158, 160 and 162, respectively, to four additional channels of EMG device 120, which thus has a total of eight channels. These additional EMG signals are processed by the EMG device and by controller 124, similar to the processing of the EMG signals from healthy arm 102. Optionally, the EMG signals from paretic arm 146 are also used by controller 124 in controlling the NMES signals. The EMG signals in paretic arm 146 may arise because the sensory-motor cortex of the patient is still capable of producing weak nerve impulses in paretic arm 146, even if these nerve impulses are too weak to cause the paretic arm to move. By timing the NMES signals to the corresponding EMG signals in the paretic arm, the paretic arm can move in response to the attempts of the patient to move it, providing kinesthetic feedback to the patient. Alternatively or additionally, EMG signals in paretic arm 146 may be induced by moving paretic arm 146 passively, for example, by a robot arm as discussed below in describing FIG. 3.

Optionally, controller 124 also uses other information in controlling the strength of the NMES signals. For example, the healthy arm has a sensor 164, for example a strain sensor, which measures the degree of bending of the elbow, and a sensor 166 which measures the degree of extension of the fingers, while the paretic arm has similar sensors 168 and 170.

Figure 3:
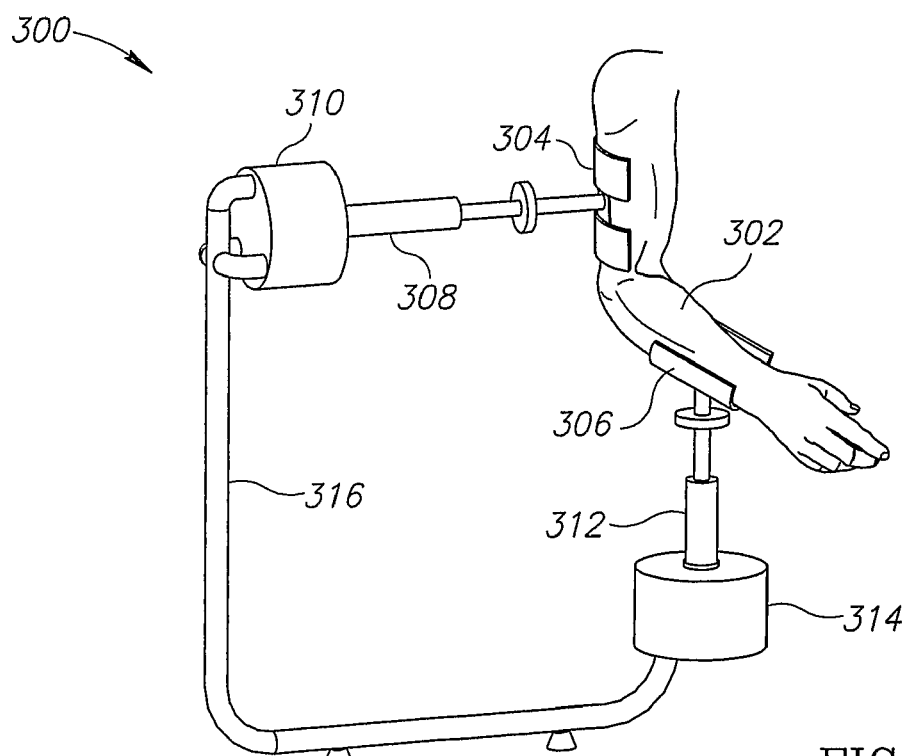
FIG. 3 is a schematic drawing of an arm attached to a robot arm, according to an exemplary embodiment of the invention.

The sensors feed into a unit 172 which processes the sensor data to determine the bending of the arm and fingers, and this information is conveyed, for example, by cable 174, to controller 124. Optionally, unit 172 and controller 124 are part of a single control unit. Optionally, sensors are used only with one of the arms. Optionally there are other sensors which measure other aspects of the arm and hand position, particularly if EMG and NMES are used with additional muscles. A variety of other types of sensors are additionally or alternatively used for measuring the arm or hand position, for example, the arm is fitted to a robot arm which has such sensors to measure its own state, as shown in FIG. 3 which will be described below. Or, LEDs are attached to key points on the arm and hand and their location tracked with a video camera, or magnetic field sensors are attached to key points on the arm and hand, and an external magnetic field and/or field gradient imposed. Other methods will be apparent to those skilled in the art of sensing the position and orientation of body parts.

The position of the paretic arm can be used, for example, as negative feedback to the NMES signals. During the course of rehabilitation, as the patient's own nerve impulses become stronger and/or more effective, for example distinguishing better between antagonistic pairs of muscles, the NMES signal can be reduced while producing the same arm motion. This kind of feedback can also be used within a given rehabilitation session. For example, if the patient is momentarily having trouble continuing to move his/her arm, the NMES amplitude is momentarily increased, until the patient is able to start moving his arm again. Optionally, in this case, the controller distinguishes between the patient simply resting, and the patient trying unsuccessfully to move his arm, for example by looking at EMG signal levels in the paretic arm.

The position of the healthy arm can be used, for example, to supplement the EMG signals from the healthy arm, as a measure of the degree of contraction of the muscles in the healthy arm. Alternatively or additionally, the data on position of both arms can be used to monitor the progress of the rehabilitation of the patient.

Robotic Actuator

FIG. 3 shows an arm 302, which could be either the healthy arm or the paretic arm in FIG. 1, attached to a robot arm 300. The upper arm is held by a holder 304, and the lower arm is held by a holder 306. Upper arm holder 304 is attached to an extendable rod 308, which is connected to a controllable ball joint 310, and similarly lower arm holder 306 is attached to an extendable rod 312, which is connected to a controllable ball joint 314. Ball joints 310 and 314 are connected to each other with a rigid connector 316. The ball joints and extendable rods include both actuators and sensors, for all their degrees of freedom, in this case two degrees of freedom for each ball joint, and one degree of freedom for each extendable rod. The sensors can sense the degree of bending of the elbow of arm 302, and the actuators can apply force to bend or unbend the elbow, and/or to resist bending or unbending of the elbow by the patient. Optionally, the actuators and sensors have more or fewer degrees of freedom, depending for example on which muscles are being rehabilitated, and optionally the robot arm is attached to additional points on arm 302, for example to different points on the wrist, hand, and fingers. Signals from the sensors and to the actuators are processed by a robot arm control box, not shown in FIG. 3.

The term robot includes other robotic actuators, for example, articulated arms.

The robot arm optionally is used in the same way as sensors 164, 166, 168 and 170 in FIG. 1. In addition, the fact that the robot arm can move in a controlled way under its own power means that it can supplement the NMES, in providing kinesthetic feedback for the patient, if used with the paretic arm. The robot arm provides a different kind of kinesthetic feedback than NMES provides, since it moves the paretic arm without causing muscles to contract under their own power, and both types of feedback are potentially useful in rehabilitation. For example, NMES may not be able to produce a smooth and accurate motion by itself, and a robot arm can help to correct and smooth the motion induced by NMES.

Optionally, both the passive and active modes of the robot arm are combined with the NMES. Movement generated by the robot arm is assisted by contraction of the muscles by NMES. When the patient moves the robot arm in an active way, the NMES signals are adjusted correspondingly.

Optionally, motion of the robot arm attached to the paretic arm is based on EMG readings in combination with motion of the healthy arm.

Exemplary Rehabilitation-Related Motions

When providing rehabilitation, various types of motion may be supported by the robotic arm. EMG may be measured and/or NMES applied during any of the motion types. The motions include, for example, one or more of:

a) Passive motion. The robot arm is moved and the patient moves with it.

b) Resisted motion. The patient moves the robot arm and encounters resistance. The resistance may be of various magnitudes and may be uniform in all directions or be directional.

c) Assisted motion. When a patient moves the robot arm, a positive feedback on arm increases the force of motion in the direction moved by the patient.

d) Force field motion. The patient moves the robot arm. Along a certain trajectory one level of resistance (or none) is encountered. Deviation from the trajectory is not allowed or meets with resistance. Motion along a "correct" trajectory can be without resistance, or possibly assisted. An increased resistance is exhibited in a volume surrounding trajectory. An even greater resistance is exhibited in a surrounding volume. A prevention of motion may be provided in an outside volume. In an exemplary embodiment of the invention, a corrective force vector is applied when not on trajectory, pointing towards trajectory. Optionally, instead of a corrective force, resistance varies as a function of distance from trajectory, thus, motion of the robot arm is naturally urged back to trajectory. Optionally, the force is applied in the direction of the path. Alternatively, the force may be a unidirectional force of resistance.

This type of motion can help train the patient in a desired motion.

e) Mirrored motion. Motion of the robot arm is required to mirror the trajectory of motion of a different element, for example for dual limb rehabilitation.

f) Free motion. Patient moves the robot arm in any way he desires, possibly receiving feedback. As the patient (or therapist or helper) moves the robot arm, a device may record it (e.g., motion and EMG) for future playback. In a playback mode the prerecorded motion (or path and optionally EMG/NMES) is optionally reconstructed using other modes. Optionally, the recorded path is modified (e.g., smoothed), for example automatically or manually.

g) General Force Field. A force field and/or an assistance field is defined which is not related to any particular trajectory. For example, a range of trajectories may be allowed to be practiced by a user, or a real or virtual situation simulated (e.g., water, areas with obstacles).

h) Local force field. A force field which is applied to only a small locality and/or only in one or two dimensions.

i) Restricted motion. One or more points of the body of a subject are supported or prevented from moving. Optionally, the angles between such points and the moving points on the device are measured. In one example the elbow is locked with a dedicated harness allowing only a shoulder motion. In some embodiments, the restriction is partial and/or is provided by a movable element (e.g., an arm).

j) Initiated Motion. The patient initiates the motion (e.g., a 1 cm motion or 100 gram force) and the robot arm completes or helps the patient complete the motion in space. The completion may be of a whole trajectory or of part of a trajectory. The completion optionally includes stimulation using NMES. The initiation optionally includes detected EMG, even if actual motion is not detected.

k) Implied motion. The robot arm begins the motion and the patient completes it. The robot arm may assist the rest of the motion in various manners (e.g., by changing to one of the modes described herein after the motion starts). If the patient fails to pick up the motion, the robot arm may generate a cue, for example an audio reminder. Different parts of a single motion trajectory may each have a machine initiation definition. Optionally, if a patient is too slow in moving, the robot arm begins the motion. Optionally, the EMG of the assisted motion is detected and used to generate NMES for the user completed motion. Optionally, a series of templates are stored for different motions of the patient and a template is elected for generating NMES based on a matching of the initial EMG portion thereof.

l) Cued motion. The patient receives a cue from the system before motion is supposed to begin, for example, motion according to a different mode. The cue can be, for example, vibration of the robot arm, stimulation pads on the skin, audio or visual cue. In some embodiments of the invention, the strength of the cue and/or its timing and/or other ongoing activities (e.g., a visual display and game) are used to help train the coordination between different modalities, for example, hand-eye coordination. A motion cue can be used to train a kinesthetic sense.

m) Teach Mode. The robot arm is taught a motion. In one example, a therapist performs a motion and motion parameters at each point are recorded and can then be used for an exercise. Another way of teaching the system is to follow a path that the therapist traces with his/her own motion. The therapist may use the controller to indicate a point to be taught or a continuous mode may be defined by which an entire trajectory is learned. Optionally the path and points are edited before replay. Optionally, the paths are processed, for example, by smoothing or identifying motion points, before playback. Optionally, the teaching includes teaching which EMG signals to expect and/or which NMES to apply. For example, a healthy arm can be stimulated with NMES during teaching so that the NMES sequence be correctly configured for the paretic arm. In one example, the patient completes the motion with the healthy arm as instructed and the NMES is modified to until the patient says that it matches. Alternatively or additionally, the patient performs the motion he feels the NMES is urging him to do and the desired motion is modified to match the actual completed motion, optionally with smoothing and/or other processing.

Thus, in some embodiments of the invention, the robot arm can provide one or more of Isokinetic, Isotonic and Isostatic exercises.

It should be appreciated that a definition of a trajectory which the robot arm is to follow can include speed parameters. For example, a user may be assisted, or urged, or expected, to move the robot arm at a certain speed. The speed may be, for example, absolute or relative (e.g., requiring a uniform speed or the speed to match a non-uniform profile). When converting EMG to NMES, the conversion may include slowing down of a motion. Optionally, slowing down includes one or more of reducing the number of stimulations to a muscle, amplitude of stimulation to a muscle and temporal spacing between stimulations to a same (at same or different locations) and/or different muscles. Optionally, motions at multiple speeds are learned so that a speed conversion factor can be determined for different muscles.

Optionally, an angular trajectory is defined, which places constraints on an angular orientation of the robot arm. In some embodiments, the constraint is one dimensional. In others it is two or three dimensional.

Speed, angles and spatial trajectories in a particular rehabilitation scenario may each belong to a different one of the above motion types. For example, spatial trajectory may be of a force field type, while speed trajectory is free or assisted. The type of trajectory and/or its parameters may also vary along the trajectory, as a function of time and/or as a function of previous performance. For example, a smaller assistance at a later part of a trajectory may be provided for a type of motion which was properly (or better than expected) executed in an earlier part of the trajectory.

Trajectories may be absolute, for example, defined as a function of a resting point or a different point on the robot arm. In other embodiments, the trajectories are purely relative, for example, requiring a patient to move an arm in a straight line, regardless of starting point. In other embodiments, a trajectory is partially relative, in that once motion starts, this determines the shape of the rest of the trajectory, for example, a start of a trajectory indicating if a patient is standing or sitting, and thus, what type of hand motion is expected.

In some embodiments, such as described below, where multiple points are defined, the trajectories of each point may be of different types. In some embodiments, what is defined is a trajectory as a function of two or more points. For example, if two points are used to define an elbow configuration (e.g., angle between bones), the trajectory constraints may be defined on the motion of the elbow. Such motion may be relative in space (e.g., a comparison of the two points) and not absolute (e.g., compared to a device reference point). It should be noted that in some embodiments of the invention a tensor or tensor field is provided, as each point in space can have associated with it a speed, a force and/or a rotation, all of which can be scalar or a vector.

In some embodiments of the invention, different modes are defined for different parts of a trajectory or for different parts of space (e.g., for a particular arm). Optionally, a mode may be triggered based on the actual performance. For example, if motion velocity is below a certain threshold, a more assistive mode is provided. Similarly, a pause of over a threshold may imply a more assistive mode. An exact motion may imply a less assistive mode.

Paretic Only Arrangement

Figure 4:
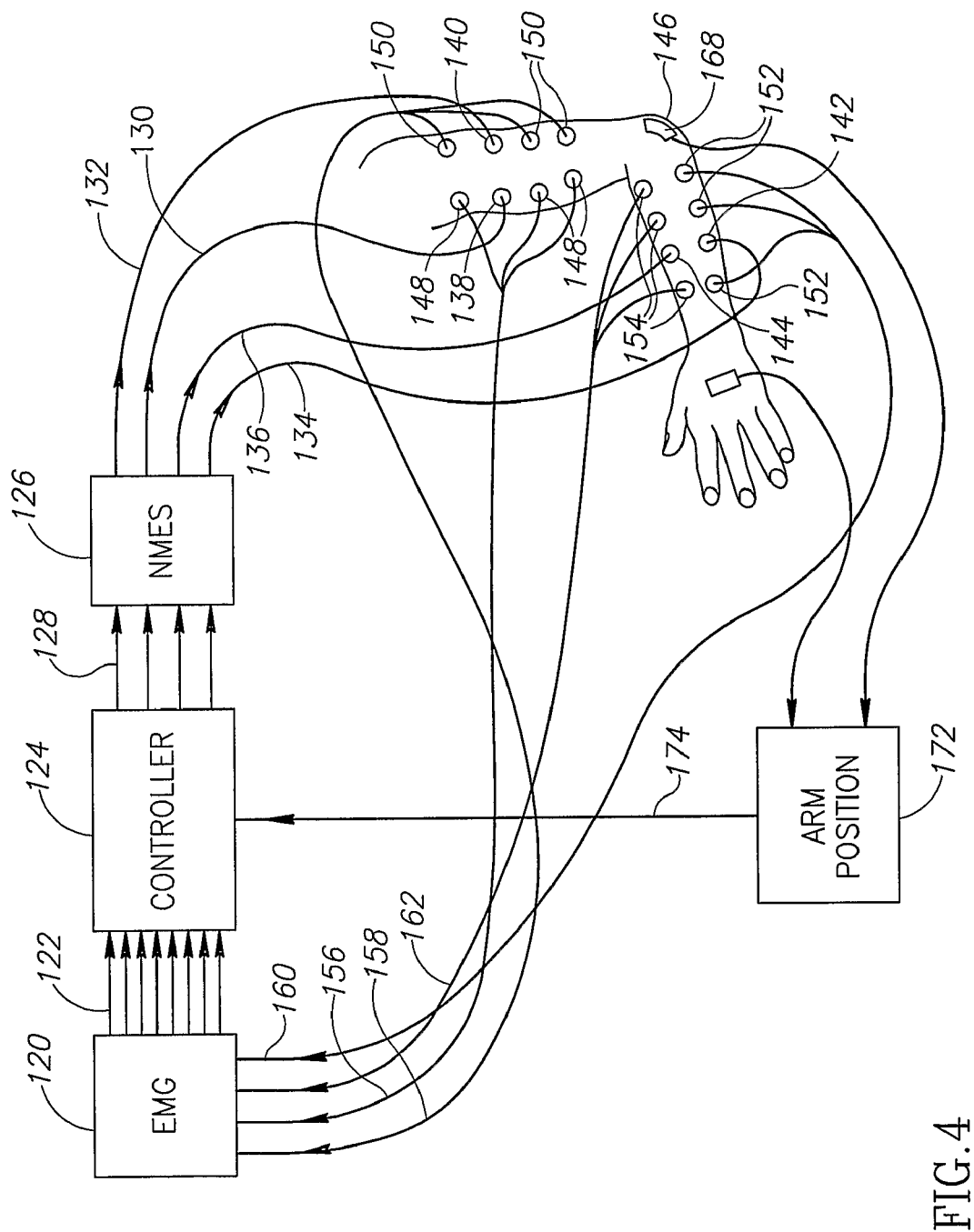
FIG. 4 is a schematic drawing of a paretic arm with NMES electrodes and EMG electrodes, nerve signals from brain, and a signal processing unit, according to a different exemplary embodiment of the invention than FIG. 1.

FIG. 4 shows an arrangement according to another exemplary embodiment of the invention, in which only a paretic arm 146 is used. As in FIG. 1, there are EMG electrodes 148, 150, 152 and 154, attached respectively to the biceps, triceps, flexors and extensors of the paretic arm, three electrodes for each muscle, and the EMG signals are conveyed along cables 156, 158, 160, and 162, to an EMG device 120, which, after preliminary processing, transmits the signals to controller 124. As in FIG. 1, controller 124 uses the EMG signals in determining the amplitude and timing of NMES signals transmitted by NMES device 126, which stimulate the biceps, triceps, flexors and extensors of paretic arm 146 through NMES electrodes 138, 140, 142, and 144. Optionally, EMG signals detected in an upper portion or on one muscle of the arm are used to anticipate desired motions (and thus NMES) of other muscles/lower portion. Optionally, one or more motion templates are stored that contain this information. Optionally, such anticipation is used to better synchronize the application of NMES signals to the patients own nerve signals (sensed at a small delay as EMG). Such synchronization can include early application of a NMES signal, for example, based on an EMG detected in one motion, an early NMES signal is applied at a later motion, before an EMG is sensed. Optionally, NMES signals are used to lower the relative threshold of sensitivity of one or more muscles and/or nerves. Optionally, such a NMES signal is a white-noise type signal, optionally sub threshold.

In an exemplary embodiment of the invention, the NMES signals transmitted by NMES device 126 in FIG. 4 are not strong enough, in themselves, to cause paretic arm 146 to move significantly, and this is optionally also true in FIG. 1. But the NMES signals, together with the patient's own nerve impulses, are strong enough to cause the arm to move. Thus, the paretic arm only moves when the patient tries to move it, and the kinesthetic feedback provided by the motion further encourages the development of alternate pathways for nerve impulses in the patient, or alternate locations in the motor cortex to originate nerve impulses to the same muscles, eventually enabling the patient to move the paretic arm by himself. This may be particularly useful when the motion involves a coordinated sequence of contractions of more than one muscle. Optionally, in the course of rehabilitation, the NMES signal is lowered, as less NMES signal is needed in order to allow the patient to move the paretic arm. In other embodiments, the NMES signal is strong enough on its own. Optionally, after some successful motions, the amplitude of the NMES signal is reduced.

Optionally, in the absence of nerve impulses from the patient's motor cortex, the NMES signals are between 100% and 120% of the amplitude needed to produce motion for an average healthy subject, or for an average paretic patient, or they are adjusted to that level for a particular patient. Alternatively, they are between 120% and 140% of that amplitude for any of these people, or between 80% and 100%, or between 60% and 80%, or less than 60%. Optionally, for any of these people, the NMES signals are between 100% and 120% of the level needed to produce motion in the presence of nerve impulses from the motor cortex when the person makes an effort to move, or between 120% and 140%, or between 140% and 200%, or greater than 200%.

Optionally, the NMES is targeted to a part of the muscle with at least as much spatial precision as an average healthy subject is able to achieve when voluntarily directing nerve impulses to that muscle. Alternatively, the NMES is targeted with less than this much precision, but with at least half this much precision, or with less than half this much precision, but at least one quarter this much precision, or with less than one quarter this much precision. For example, the NMES signals may be selectively applied to a particular muscle, optionally with a precision of better than 10 mm, 5 mm, 2 mm or better. Optionally, implanted electrodes are used to achieve better temporal resolution. Optionally, such implanted (or external) electrodes are used to sense areas of muscles which actually receive nerve signals (e.g., as evidenced by EMG signals or by directly measuring nerve signals). Optionally, rehabilitation first or separately focuses on such areas to which a cortical pathways is known to exist.

Examples and Variations

Characteristics of the procedure illustrated in FIGS. 1 and 4 can be varied to adapt to the needs of the patient, in order to facilitate rehabilitation. Several examples are given below.

The EMG and NMES need not use the four muscles shown being used in FIGS. 1 and 4, but could include more muscles, or fewer muscles. Optionally, only the biceps and triceps are used initially. Then, once the patient has gained some ability to use the biceps and triceps effectively, the flexors and extensors are added to the EMG and NMES channels. These four muscles are basic to gross control of the arm, in addition to other muscles such as the pectorals and the deltoids. Later, individual fingers are added, and/or other wrist and hand motions, to improve fine motor control. For rehabilitation of body parts other than the arm, of course, other groups of muscles are selected.

The amplitude of NMES optionally varies depending on feedback from various sources, and depending on the immediate goal of the rehabilitation program. As mentioned previously, the NMES signal is optionally decreased as the patient recovers the ability to generate nerve impulses and move his muscles by himself. Alternatively, if the immediate goal is the strengthening of atrophied muscles, the amplitude of NMES is optionally increased as the muscle gets stronger, and can benefit from more strenuous exercise. In this case, the arm is optionally made to move against a restraining force, for example a weight or a robotic arm, which is increased as the muscle gets stronger, so a stronger NMES signal is required in order to move the arm by the same amount.

In addition to using kinesthetic feedback to encourage the development of alternative pathways for nerve impulses, as discussed above, other kinds of feedback are optionally used to help the patient learn how to control his muscles more effectively. For example, seeing the movement of the arm, when his nerve impulses are supplemented by NMES stimulation, can help the patient adjust his efforts to move his arm. Similarly, such feedback for conscious learning by the patient can be provided by a device, such as the robot arm in FIG. 3, which measures and records the motion of the arm, and by the processed EMG signals. For example, the patient can try to make the EMG signals from the paretic arm more closely resemble the EMG signals generated by the healthy arm when it is performing the desired movement, or he can try to make the EMG signals from the paretic arm more closely resemble some template, perhaps developed from examining recorded EMG signals from the healthy arm, or from paretic arms of other patients who have undergone similar rehabilitation. Optionally, the robot amplifies actual motion of the arm, to make it more visible to the patient and/or therapist.

In the arrangement shown in FIG. 1, if the patient's other arm is used as the healthy arm, then optionally the patient tries to move both arms synchronously, in mirror image movements. The NMES signals, optionally based on the EMG signals of the healthy arm, allow the paretic arm to move, and since the patient is attempting to move both arms in synchrony, he receives kinesthetic feedback from the paretic arm, which helps promote the development of alternate pathways for nerve impulses. In some embodiments of the present invention, movement of the paretic arm to mirror movement of the healthy arm is assisted, in part or in whole, by the robotic arm 300.

Optionally, the NMES signals are adapted to the capability of the paretic arm. For example, if the muscles in the paretic arm are incapable of responding as rapidly as normal to the NMES, then the NMES signals are optionally slowed down, or high frequency components are reduced or removed. As the muscles recover the capability of more rapid response, the NMES signals are sped up again. The speed of the NMES signals is either adjusted automatically, in response to sensor data on movement of the paretic arm, or manually by the therapist, optionally using such sensor data to evaluate the patient. If a robotic arm is used in coordination with NMES to help move the paretic arm, the motion of the robotic arm is optionally slowed down together with the NMES. Even if the robotic arm is used to help move the paretic arm without NMES, the motion of the robotic arm is optionally slowed down if, for example, this will help the patient to make a greater contribution to the motion with his own nerve impulses, or will be useful for some other reason in rehabilitation.

Figure 5A:
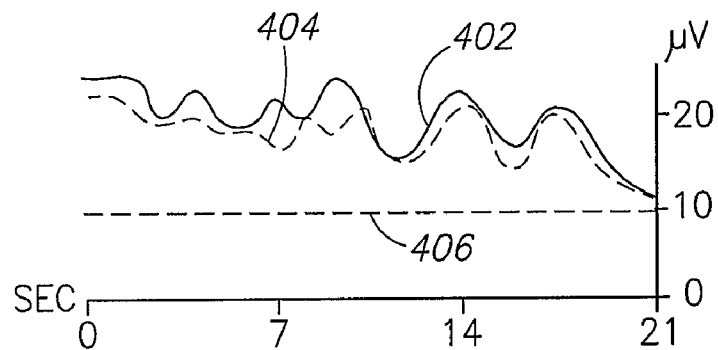
FIGS. 5A-5G are a time sequence of plots of EMG signals from flexor and extensor signals, at different times during rehabilitation, according to an exemplary embodiment of the invention.
Figure 5B:
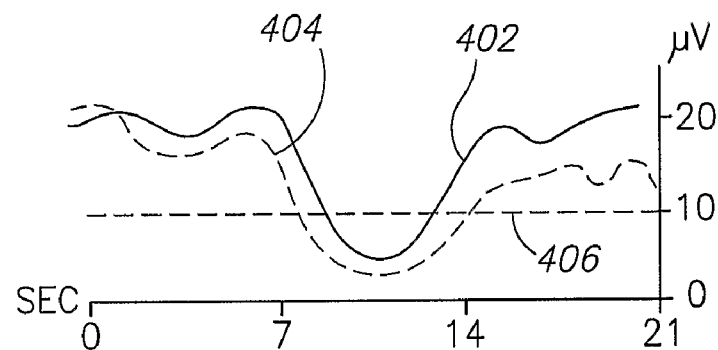
Figure 5C:
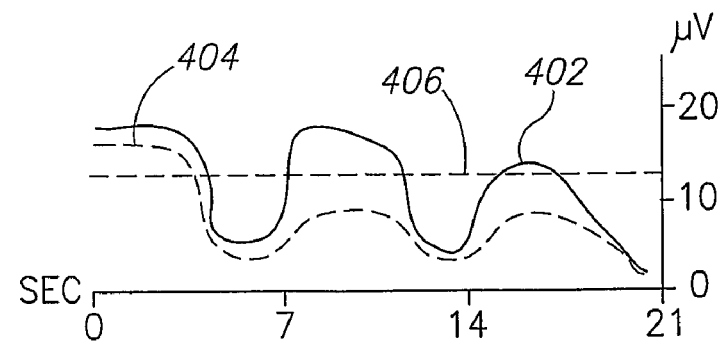
Figure 5D:
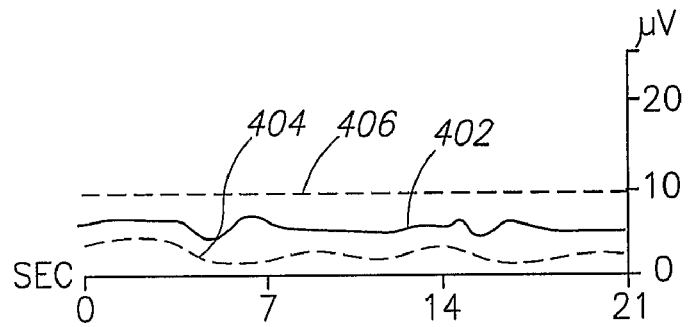
Figure 5E:
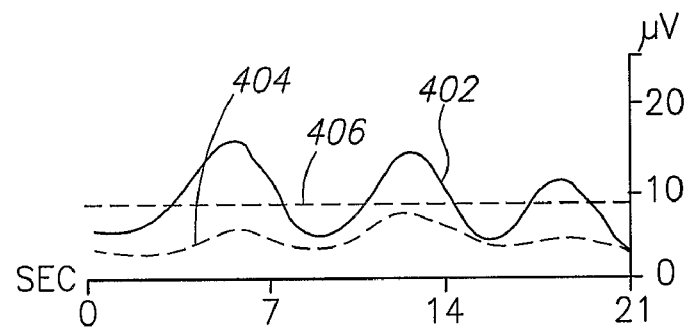
Figure 5F:
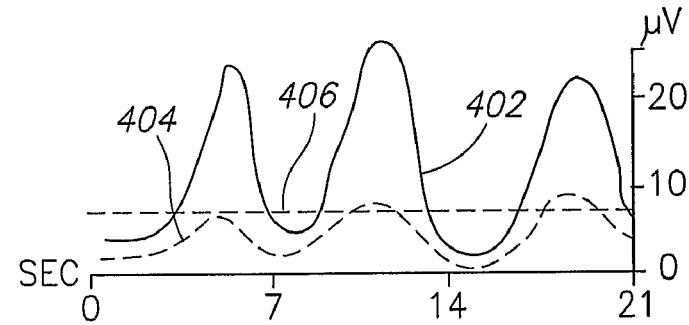
Figure 5G:
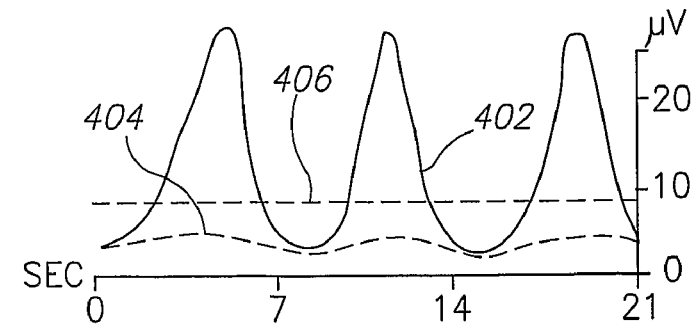

FIGS. 5A through 5G illustrate a procedure for rehabilitating a patient who has a problem that is common following a stroke in the somato-motor cortex—the failure of the patient's nerve impulses to distinguish adequately between two muscles that form an antagonistic pair, such as the biceps and triceps, or the flexors and extensors. As shown in FIG. 5A, the EMG signal 402 from the flexors, and signal 404 from the extensors, when the patient attempts to open and close her hand, are strong enough to cause both muscles to contract, since they are above threshold level 406. But both muscles contract at the same time, so that they work against each other, and the hand exhibits very little movement. First, the patient learns to decrease the overall activity of both the flexors and extensors, below the threshold for contraction, as shown progressively in FIGS. 5B, 5C, and 5D. Then, as shown in FIGS. 5E, 5F, and 5G, the patient is taught to increase the activity of the extensors, while keeping the flexors relaxed. This is done, for example, by applying NMES to the extensors, increasing kinesthetic feedback, when patient tries to contract the extensors.

Alternatively or additionally to NMES, electrical or other stimulations (e.g., vibrations) may be used to provide feedback to a patient. For example, vibration amplitude and/or frequency (e.g., as applied at the surface of the relevant muscle) may serve to supplement damaged kinesthetic sensing of tension in a muscle. Optionally, the feedback is based on measured parameters, such as tension, EMG and/or shaking. Alternatively or additionally, the feedback indicates what the patient should be feeling if a motion and/or muscle contraction are actually happening.

Exemplary Rehabilitation Methods

To summarize, listed below are some of the rehabilitation methods that can be used in some embodiments of the invention, including those discussed. It should be noted that a robot is not strictly needed for several of these modes. Optionally, a wireless position sensor is used to measure position instead of or in addition to a robot. Similarly, while optionally some motions are mediated by a robot, other motions may be unmediated, for example being performed during the day while not connected to the robot.

1) Record EMG in healthy arm and apply similar pattern of NMES to paretic arm, in real time or not (e.g., at a delay, as a combination of multiple measurements). Optionally, a delay is used to allow the patient to transfer his attention from the healthy arm to the paretic arm, for example, 1 second or less than 10 seconds.
2) Adjust NMES amplitude to supplement nerve impulses in paretic arm, as measured by EMG in paretic arm. Optionally, the NMES amplitude is selected to achieve a desired tension in the stimulated muscle.
3) Target NMES to sections of paretic arm where EMG is weak. Optionally, if a plurality of electrodes are implanted, only those electrodes corresponding to weak EMG areas are electrified. Alternatively or additionally, the amplitude of stimulation and whether it is sub- or supra-threshold depends on the weakness of the EMG (e.g., as compared to EMG from a healthy arm).

4) Slow down NMES to adapt to slow response time of paretic arm.
5) Have patient move both arms together, in mirror image, while applying NMES based on EMG in healthy arm.
6) Have patient move both arms together, not in a mirror image, and/or in a cyclical motion 180 degrees out of phase, while applying NMES based on (but modified from) EMG in healthy arm.
7) Base NMES on average (or other processed) EMG over multiple repetitions of movement by healthy arm, for example, 2, 3, 5, 10 or an intermediate or larger number of repetitions.
8) Sense position (and/or EMG) of paretic arm and use negative feedback for NMES; optionally using EMG of paretic arm to distinguish inability to move arm from intentional resting.
9) Record sensed position of healthy arm as a function of time while recording EMG signals, then apply corresponding NMES to paretic arm when paretic arm is in a corresponding position. Optionally, the recoding is binned according to motion type, exercise type, speed and/or type of resistance/interaction with a robot.
10) Use robotic arm to move healthy arm in a desired pattern, detect the resulting EMG signals generated passively in the healthy arm, and use them as a basis for NMES applied to paretic arm to produce corresponding motion.
11) Use robotic arm and/or NMES to move or assist moving paretic arm, matching to measured position of healthy arm. Optionally, the selection of assistance by NEMS or a robotic device and/or the amplitude of the assistance is varied, for example randomly, between exercises.
12) Use robotic arm to measure resistance of paretic arm to motion, thereby determining whether failure of paretic arm to move is due to failure of muscle to contract, or failure to differentiate between antagonistic pairs of muscles; optionally adjust NMES accordingly.
13) Use robotic arm, with or without NMES, to assist moving paretic arm, slowing down robotic arm to match capability of paretic arm.
14) Use robotic arm to work against muscles of paretic arm, with or without NMES, optionally adapting force to capability of paretic arm.
15) Use EMG of paretic arm to teach patient to better control paretic arm, optionally including better differentiating between antagonistic pairs of muscles.
16) Use a combination of NMES and mechanical actuation to strengthen muscles. In an exemplary embodiment of the invention, the NMES is used to ensure that a muscle is being used. Optionally, the exercise is selected so that the NMES actuated muscle portion is not sufficient for carrying out the exercise. Optionally, one or more tension sensors or EMG sensors are used to assess the muscle activity. Optionally, the actuator is used to apply resistive force to movement during an exercise. Optionally, additional NMES electrodes are provided for use during exercise. Optionally, NMES is activated at a higher power and/or more often during exercise, as compared to triggering modes that are used during daily activities.

Particular Examples Relating to Recording, Stimulation and Assessment

Figure 6:
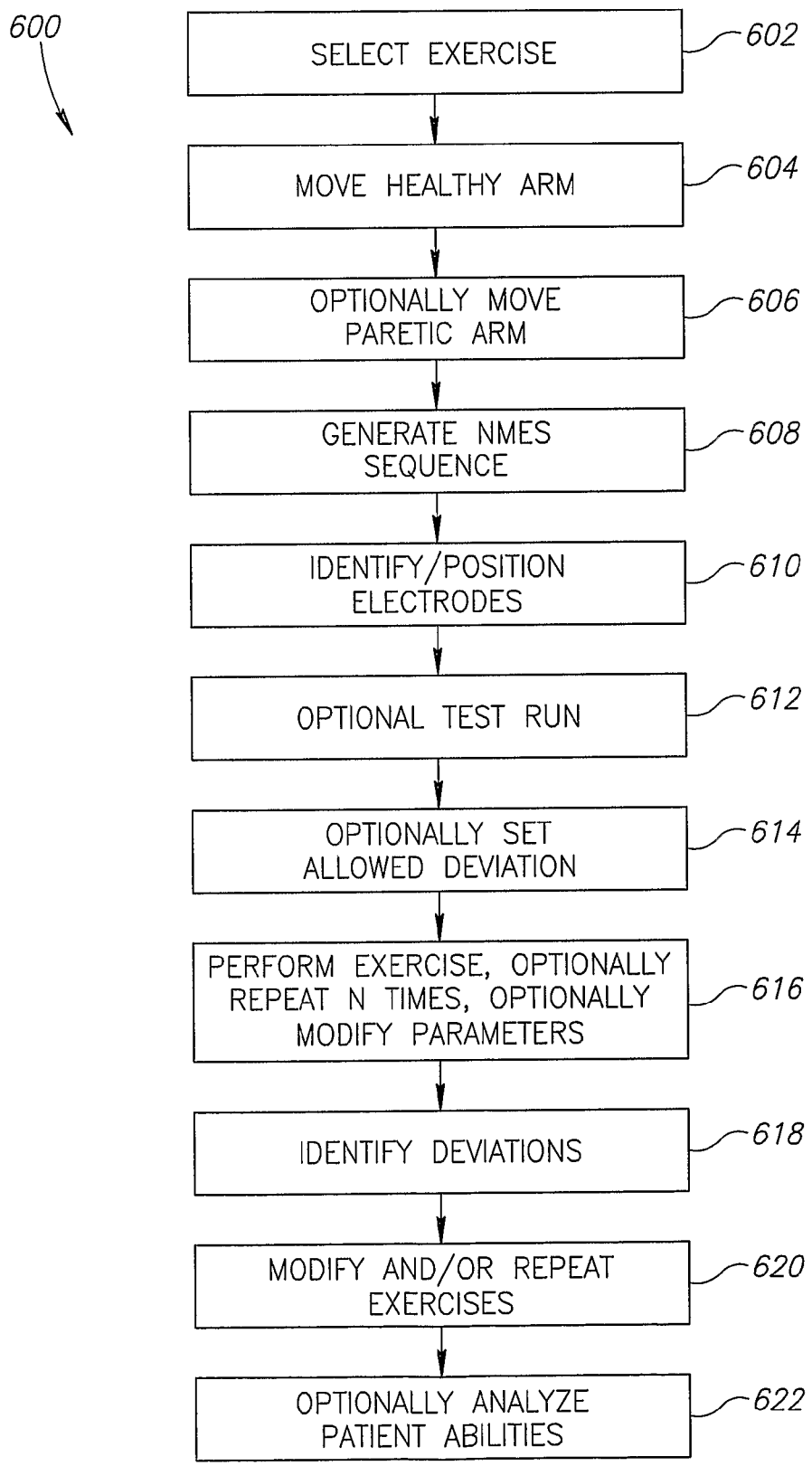
FIG. 6 is a flowchart of a method of using a robotic actuator to define and optionally assess patient improvement, in accordance with an exemplary embodiment of the invention.

FIG. 6 is a flowchart 600 of a method of using a robotic actuator to define and optionally assess patient improvement, in accordance with an exemplary embodiment of the invention.

At 602, an exercise to be performed by the paretic arm (or other body part) is optionally selected.

At 604, the healthy arm is optionally put through the motion, by the patient, with the robot or other position sensor measuring the motion, with EMG measured. Optionally, a force field or other feedback (e.g., vibrating pads) is provided to guide the motion. Optionally, measurements of EMG right after a (manual) correction are ignored, for example, being supplemented or replaced by measurements from a different repetition. The motion may be repeated, for example, to generate an average EMG signal.

At the end of the motion, an EMG sequence is optionally generated, which includes EMG signals (e.g., amplitude) measured, at different times and different positions for different muscles. Optionally, the measurements include at least 3, at least 4, at least 6 or at least 8 different muscles or muscle parts. The muscles may be arranged to control, for example, at least 1, at least 2, at least 3 or more joints. The duration of the motion may be, for example, at least 1, at least 10, at least 30, at least 60 or more seconds and may include, for example, at least 10, 20, 40 or more individual muscle activation events.

Optionally, the motion is interactive with the robot, for example the robot providing feedback on correct motion, uniformity of speed, desired rest periods and how much force to apply (it being noted that a paretic arm may need more force applied (in thought) than a healthy arm in order to achieve a same motion).

Optionally, the motion comprises only part of a complete exercise, which is put together by combining NMES sequences generated for each motion portion.

Optionally, at 606, a paretic arm is moved (or guided, e.g., with the patient attempting to perform a motion), so that a baseline paretic EMG is measured. As noted above, NMES may be made stronger or weaker for areas that have some residual EMG measurements thereof.

Optionally, the motion is resisted by the healthy arm, in order to generate signals for teaching the paretic arm to resist forces. Optionally, the resisting signals are inverted (e.g., the muscles activated switched) and used as a signal for motion.

In an exemplary embodiment of the invention, the paretic arm is used instead of the healthy arm. In one example, the robot is used to learn the effect of the electrodes. One way of doing this is to stimulate the NEMS electrodes and measure the resulting motions or motion sections. This may appear to be unstructured motion. Optionally care is taken to prevent overstraining of muscles, for example, using tension sensors. Such learning optionally includes one or more of vector of motion, applied force, minimal effective stimulation time and strength which causes tetanus. Optionally, the robot experiments, by providing NMES sequences (e.g., defined as a baseline set) and determining the actual affected movement. The patient may be instructed, for example, to ignore the stimulation, to fight the stimulation and/or to flow with the stimulation. Optionally, a process of iterative enhancement is carried out, with the NMES sequences being continually modified so as to improve the movement, for example, bring the movement closer to a desired or best possible movement.

The result of the learning can be a set of NMES segments that correspond to movements segments, which segments can be used as primitives when generating more complex NMES sequences.

At 608, a NMES sequence is generated from the EMG signals and from the desired motion parameters. Optionally, the NMES sequence is modified (and optionally the exercise as well) to take into account the ability (e.g., spatial, force and/or temporal) resolution of the stimulation electrodes.

Optionally, the sequence is processed, for example, smoothed and/or with possible artifacts removed.

Optionally, the healthy arm is used for selecting the sequence of activation of NMES, with the amplitude, relative timing and/or relation between opposing muscles being selected based on other reasoning, for example, previous testing of the patient.

Optionally, the NMES sequence includes a time line and trigger signals, for example, an identification of an EMG signal that if sensed causes a certain (absolute or parametrically defined) NMES signal with a delay.

At 610, one or more relevant stimulation electrodes are identified and/or positioned. For example, if a plurality of wireless electrodes are implanted, only some of these electrodes are needed. In another example, some electrodes may not work or may not have sufficient residual EMG associated with them. Optionally, the NMES sequence and/or desired exercise are further modified in response to electrode availability.

At 612, a test mm is optionally performed, as result of which the NMES sequence may be further modified.

In an exemplary embodiment of the invention, a NMES sequence is generated to be optimal or near optimal. Optimality may be difficult to achieved, for example, due to noise, the patient's disorder and/or lack of suitable electrodes and/or resolution of control. A threshold value representing how near to optimal is expected for various exercises, may be provided. Optionally, a best motion (e.g., to within 10% or expected ability) is considered near optimal.

In an exemplary embodiment of the invention, good motion is identified as motion consisting of smooth motion. Optionally, the motion is considered better if it includes fewer NEMS/EMG events. Optionally, a ⅔ power rule is expected. Optionally, minimum and/or maximum forces and/or accelerations exerted on the robot are detected. Such maximum and minimum values may be set, for example, by a healthy arm or by learning a motion of a therapist.

In an exemplary embodiment of the invention, the robot or other means are used to measure the force exerted by the patient and/or its direction. For example, during a daily activity of lifting a cup, pressure sensors attached to the cup can be used to indicate to the patient (and the controller of the NMES sequence) if the grasping pressure is too slight (and cup may fall) or too high (and cup may break or tip).

Optionally, a NMES sequence is further optimized by attempting to reduce electrode power consumption (on one electrode or more, optionally as a set), while maintaining other motion parameters. This measure may be determined, for example, on multiple repetitions, for example, to assess the effectiveness of nudges.

At 614, a range of allowed deviation from the desired exercise is optionally set. This range may depend on the location in the trajectory, for example. Soft deviations, trigger conditions and/or force fields to be applied may also be set.

At 616, one or more exercises are carried out. Optionally, the exercises are repeated a plurality of times, for example, with different parameters, such as different resistance or force profiles, different speeds and/or different spatial locations.

At 618, deviations from the correct motions are identified.

At 620, exercises are repeated and/or modified. Optionally, the exercises focus on portions where the deviation was maximal. Alternatively or additionally, the exercises focus on portions which were correctly carried out. Optionally, the modification includes modifying NMES parameters, for example, one or more of amplitude, frequency, duration, envelope, delay relative to trigger and/or order. Optionally, for parts where the patient did well, the NMES is reduced or canceled, at least some of the repetitions. Optionally, the stimulations are provided in a nudge mode, to remind a patient or to assist if an expected EMG signal is not detected. Optionally, the use of implanted electrodes allows EMG signals to be measured in one region concurrently with stimulation in a nearby region. Optionally, the EMG signal is filtered to remove the effect of nearby stimulations.

At 622, the exercise results are optionally analyzed to determine the patient's current ability, for example, by providing exercises with a range of stimulation sequences and/or exercise parameters.

In an exemplary embodiment of the invention, the exercises include daily activities, such as drinking with a cup, pouring, holding an object and picking up and placing an object. Optionally, at least some of the EMG measurements and/or NMES stimulation are carried out using a portable device that minimally interferes with daily activities. Optionally, the user indicates to the device that a certain daily activity is being carried out. Logging of EMG and/or appropriate stimulation of NMES is applied. Optionally, different sequences are stored (and optionally generated exhaustively using a robotic actuator) for different body positions. Optionally, the body position is identified using a suitable sensor (e.g., a tilt sensor) on the body part, so that the sequence of actions matches the activity parameters. Optionally, the NMES sequence is interpolated between nearby taught positions.

Wireless and Portable Electrodes

As noted above, the electrodes can be provided in several configurations, for example:

(a) an electrode system integral with the robot;

(b) a set of implanted electrodes, with a wired or wireless controller and/or data logger;

(c) a set of surface electrodes with a portable controller;

(d) as part of an assist device, for example, a partial or complete exoskeleton;

(e) as part of a support platform, such as a bed or chair; and/or (f) as part of a neural prosthesis, such as the NESS H200, mentioned above, which applies NMES signals instead of, or in addition to, nerve conduction.

In any or all of these configurations, the electrodes can be used for sub-threshold alternatively or additionally to being used for supra-threshold NMES. Optionally, as a patient improves more sub-threshold and less supra-threshold NMES signals are applied. Optionally, the NMES is used to nudge and/or remind a patient to make a motion. Optionally, a patient override is provided, for example, to cancel NMES or to force full-fledged NMES.

It should be noted that the electrodes may or may not be removed after a time. For example, for spinal column injuries, there may be no neural pathways and the electrodes will remain. In a stroke victim, rehabilitation is generally desired to improve to a point where no electrodes are needed, at least not for NMES.

Optionally, the electrodes are provided in conjunction with a brain stimulator, for example, synchronizing the brain stimulation to muscle stimulation (optionally with a suitable delay) or using the brain stimulator to provide feedback from the device.

Also as noted, one or more feedback devices may be provided, for example, vibrating pad, displays, voice outputs, for example, for providing instructions or feedback to the user. An exemplary instruction is "Relax, your muscles are too tense".

Optionally, one or more user input devices are provided, for example, buttons, knobs or a touch screen. Optionally, a gesture input is used. Optionally, speech input, personalized to the user and/or a therapist, is used. Optionally, EMG signals from another limb or body part are used as a trigger to initiate motions. As noted above, the actual motion may be modified, for example, based on body position, limb position and/or relative positions of body parts. Optionally, a BCI (brain-computer interface) is used, for example, a set of electrodes (e.g., EEG) embedded in a baseball or a swimming cap.

In an exemplary embodiment of the invention, a robot/actuator is used to train a system for BCI. For example, the robot can be used to sense deviations between a command that was generated, and its result. For example, in BCI systems where the command is a high-level command, the sequence optimization can be as described herein. For example, in BCI systems where low-level motor commands are generated, a match between the individual commands and small segments of NMES may be generated. Optionally, the positioning of electrodes of the BCI and/or processing of the BCI signals are modified to take into account the possible NMES sequences and/or effects.

Optionally, the device includes a rechargeable battery. Optionally, a wireless or wired (when plugged in) link is provided, for example, via telephone, wireless LAN or WAN or cellular telephone. The link may be, for example, to a remote database, to a data monitoring station and/or to a caregiver who may provide live or delayed live feedback to the patient. In an exemplary embodiment of the invention, when a patient does a daily activity and performs well, performs badly, and/or according to any other preset trigger condition, the caregiver is notified and may provide feedback.

Optionally, when operated as a prosthesis, the device may be programmed to provide ongoing rehabilitation during use. For example, during certain times of day and/or after suitable warning, a patient may be urged to carry out a series of exercises.

In an exemplary embodiment of the invention, the robotic actuator is used to program motions, motion sets, EMG signals and/or tested NMES signals for a neural prosthesis. Optionally, the repeatability and ability to indicate error and splice signals from multiple attempts is utilized for programming the prosthesis. Optionally, exact repetitions are provided using a robot (e.g., for measuring nerve signals of the kinesthetic sense), even when the patient is not attentive.

Calibration, Setup and/or Maintenance of Electrodes

The above described process may be used and/or modified to calibrate and/or set up electrodes to be used. One problem with electrodes is that their actual effect on tissue may be difficult to ascertain ahead of time. Another possible problem is that after time, the effect of an electrode may change over time, for example, due to fibrosis, muscle buildup, electrode migration, electrode breakage, improved neural activity (or degradation thereof) and/or difficulty in positioning an external electrode, such as due to movement marked location.

In an exemplary embodiment of the invention, a robotic actuator is used to assist in setting up electrode control. In one example, the location of an electrode is selected, for example, based on a location where EMG is sensed and/or when NMES has the best effect on a repeated test exercise. In another example, the signal applied to the electrode, for example, amplitude, frequency and/or length is selected based on repeated experiments with various parameters. In another example, the envelope of the signal is selected. Optionally, a same envelope is used for multiple electrodes. In an exemplary embodiment of the invention, as a patient exercises, the robot or other sensors are used to measure performance and modify the electrode setup. Optionally, as noted herein, sequences from healthy limbs are translated for use in paretic limbs, whereupon they may be tested and/or optimized using the robot/other sensors.

In an exemplary embodiment of the invention, the robot is activated when the electrodes are activated as pairs, for example, stimulating agonist muscles against antagonist muscles. In an exemplary embodiment of the invention, the performance of a pair of electrode can be monitored and/or challenged by the robot, for example, by the robot exerting force on the limb to see if the muscles with the electrodes respond (e.g., force, direction) as required. Optionally, the response of the muscles is generated without patient participation using NMES stimulation.

In an exemplary embodiment of the invention, the robot repetitive motions are used to ensure that a plurality of different motions are programmed into the controller. Optionally, the programming includes calibration of one or more position and/or acceleration sensors in a prosthesis and/or implantable electrodes. While it was described that wireless electrodes can use an external controller, optionally, each electrode or a set of electrodes share activation logic. In one example, a wireless electrode includes one or more accelerometers which can be programmed to match acceleration conditions to desired electrification and/or logging. A plurality of sense-stimulate or stimulate programs may be stored in such a wireless electrode. Optionally, an initial triggering signal is sent to a plurality of wireless electrodes to indicate a general command to be carried out and the acceleration sensing (in 1, 2, 3, 4, 5 or 6 dimensions—spatial and/or orientation) is used to decide if stimulation is needed and/or how to modify the stimulation. Optionally, this reduces bandwidth, power and/or addressing requirements from the electrodes.

In an exemplary embodiment of the invention, a personal profile of what electrodes to activate, in what sequence and when, is stored as a personalized file. In an exemplary embodiment of the invention, the electrode setup is modified as the user uses the system. For example, each time a cup is poured (or other activity which can be identified before or after the activity), a user and/or the system may have the option to indicate if the motion was acceptable, non-acceptable, better and/or worse (or other quality indications). For example, the system can apply smoothness considerations, the user may be provided with an input. Good and/or better motions may be used to select different NMES sequences. Bad results may be used to deselect sequences. Various learning methods and algorithms are known in the art which can be based on such feedback, for example neural networks and AI learning algorithms.

In an exemplary embodiment of the invention, periodic maintenance of the electrodes is performed, for example, to see they still operate as expected. Optionally, such maintenance is requested in response to multiple incorrect performances by the patient. In an exemplary embodiment of the invention, the checking comprises requiring the user to carry out a motion which the motion is sensed using the robot, optionally, using external electrodes to supplement implanted electrodes. Optionally, the recalibration checks first for moved electrodes and for electrodes whose amplitude is incorrect.

In an exemplary embodiment of the invention, some electrodes will be canceled (i.e., inactivated or removed) or their use reduced, for example, to keep in line with improvements in the patient. Optionally, electrodes are moved as needed. Optionally, the conditions under which electrodes are triggered are modified to take into account changes in the patient.

In an exemplary embodiment of the invention, the electrodes and NMES are used for gait training. In an exemplary embodiment of the invention, EMG signals from one leg are used (at a delay which may be dependent on leg motion speed and/or accelerations) to stimulate NMES in a paretic leg. In an exemplary embodiment of the invention, the combination of NMES and EMG is used to improve bi-sided coordination between limbs, for example, by compensating for lack of abilities and/or improving timing synchronization between limbs. Optionally, an EMG event in one limb is used as a NMES trigger in another limb, for example, automatically (e.g., based on a template) or for example, if a suitable EMG is not sensed at a certain location in the paretic limb within a certain time window. The healthy leg may also be used as a source of desired sequences of activations for the paretic leg and/or for a desired time/delay of EMG events, which, if not met, cause NMES events to occur. Optionally, at least some sequences are stored in the controller. Optionally, the controller and/or electrodes have associated therewith accelerometers and/or position sensors for indicating mechanical gait characteristics. It should be noted that in some patients it can be known ahead of time that input from the healthy leg must be modified before being applied to the paretic leg, for example, if one joint has a limited range of motion. In other cases, trial and error methods are used to determine a suitable mapping between limbs.

In an exemplary embodiment of the invention, the sequence of activation of NMES for various walking conditions and/or gait types are copied from a healthy leg to the paretic leg. Optionally, in paretic locations where EMG is sensed, NMES is not applied or applied at a lower amplitude. Optionally, NMES at other locations is applied at a different time and/or amplitude, to counteract the effect of lower muscle activation at some areas. Such compensation may be determined, for example, by experimentation using electrodes as described herein and measuring the effect. This may enhance the safety of patients, for example, by preventing falling. Various gait types can be trained, for example, walking, climbing, standing up and/or sitting down.

In an exemplary embodiment of the invention, external sensors are used to assess the effect of NMES. For example, pressure sensors (under the feet) can be used to detect balance of a standing person. A tilt sensor may be attached to a torso, to indicate balance maintaining. Input from such sensors may be used as feedback for the optimization process of sequences. Additional sensors may be used, for example, vision sensors which acquire images of moving body parts. Markers may be provided on the body to assist in identification.

Optionally, during calibrations, an emphasis is made on reducing power consumption. Optionally, the electrodes are recharged at the time of calibration, if they require charging. Optionally, the electrodes indicate a required charging need by providing noticeable signals, for example, repetitive short stimulation signals or stimulation at frequencies or other pulse parameters that affect nerves but not muscles.

Optionally, new sub-optimal sequences are found, as the patient physiology and/or electrode effectiveness change.

In some exemplary embodiments of the invention, the robot used for maintenance is a simple resistance robot that guides motion by resisting motion not along a certain trajectory. Alternatively or additionally, instead of a robot, a set of one or more position sensors is used, for example, position sensors read by a computer.

In an exemplary embodiment of the invention, at least some of the activities described herein are carried out at a patient's home. For example, regular monitoring of electrode and NMES effectiveness and training of new NMES sequences may be performed at home. In an exemplary embodiment of the invention, the robot includes an interactive wizard which guides the user (patient/caregiver) through the process of defining a new motion. Optionally, a library of motions is provided to serve as a starting point. In an exemplary embodiment of the invention, the wizard instructs the user to provide a sufficient number of examples from a sufficient number of starting points and with a sufficient number of repetitions and optionally provides an indication if the result of the training is satisfactory. Optionally, a link to a remote center (e.g., rehab center) is provided, for example for on-line assistance or data files. Optionally, a display of the expected motion is provided, for example by moving an actuator of the robot or using a display of graphics.

Electrode Implantation Method

Figure 7:
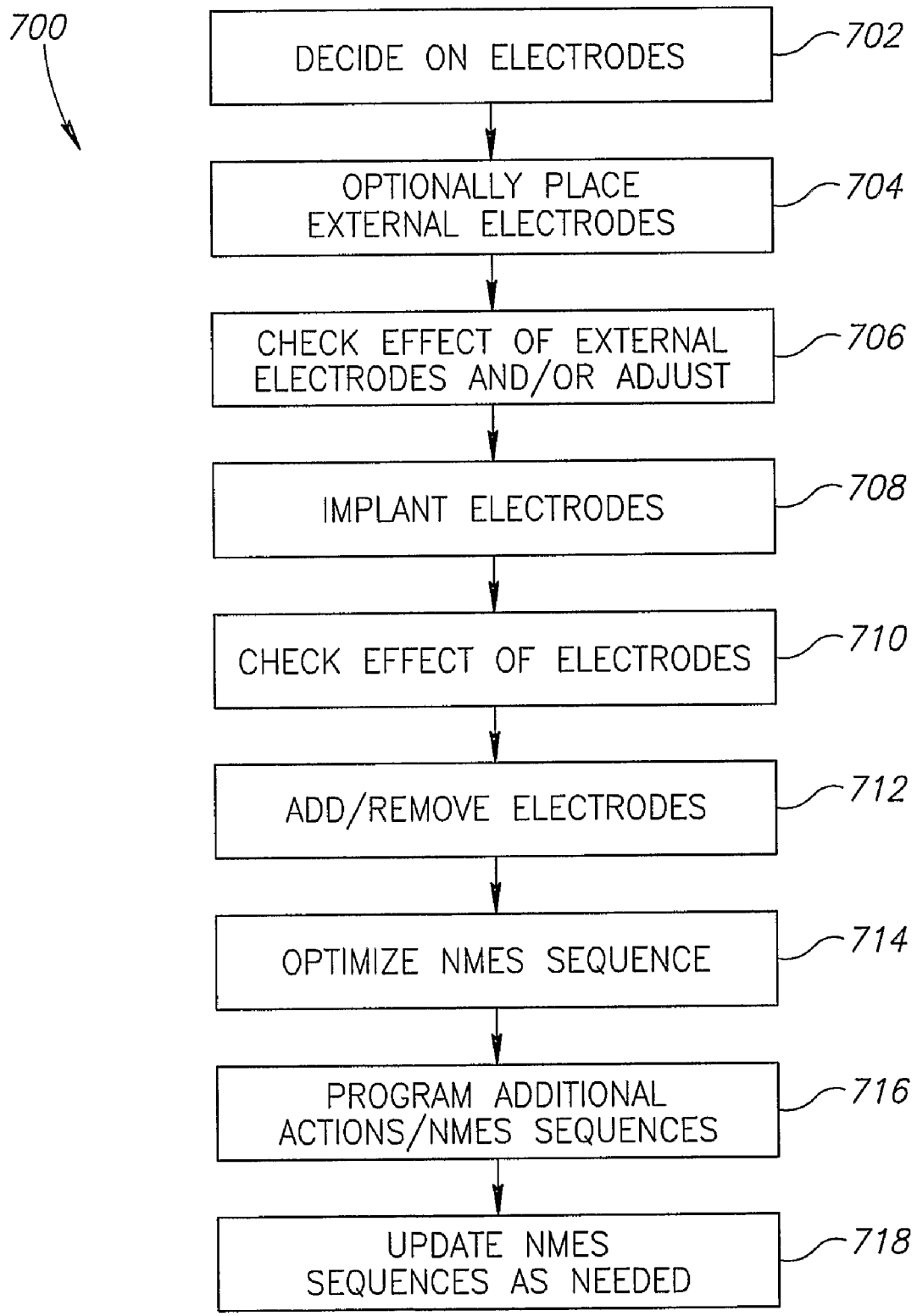
FIG. 7 is a flowchart of a method of implanting and programming implantable electrodes, in accordance with an exemplary embodiment of the invention.

FIG. 7 is a flowchart 700 of a method of implanting and programming implantable electrodes, in accordance with an exemplary embodiment of the invention.

At 702, a plurality of potential electrode locations are selected, for example, based on the physiology of the injury.

At 704, prior to implanting electrodes, one or more external electrodes may be placed at the locations. These electrodes typically have a lower spatial resolution.

At 706, the effect of the external electrodes is assessed and the positions of the external electrodes may be adjusted. Assessment is, for example, using the robot to measure movement initiated by NMES. It should be noted that the assessment may be made on small motion parts. Optionally, the robot is used to bring the paretic limb to starting locations at which the effect of NMES is to be measured.

At 708, one or more electrodes are implanted. Optionally, these electrodes are wireless electrodes.

At 710, the effect of these electrodes are determined, for example, using a robot or other sensors, such as a vision system or tension measurement.

At 712, one or more electrodes are optionally added or removed.

At 714, the NMES sequence for the electrodes is optimized, for example as described above. In an exemplary embodiment of the invention, optimization described herein may use optimization and search methods known in the art, such as hill-climbing, linear programming methods, trial and error, statistical experimentation and shotgun approaches.

At 716, additional activities and/or NMES sequences may be programmed, for example at the patient's home, for example, by the patient. Optionally, the robot includes a programmer for wireless implanted electrodes.

At 718, NMES sequences are updated, for example periodically, for example as described above.

Pain

In some cases, implanted or external electrodes are used to block and/or mediate pain. In an exemplary embodiment of the invention, the methods described herein are used to optimize or reduce the use of power in such electrodes. In one example, movements under support of a robot are used to learn when pain is to be expected. The wireless electrodes are then programmed to be activated only when needed, for example, using an accelerometer to sense orientation, or based on an expected effect of NMES sequences (or EMG or nerve sensing) by those or other electrodes. Optionally, the programming is local, for example, each electrode programmed to respond to its local sensing and/or activity. Alternatively or additionally, one electrode responds to the actions and/or sensing of other electrodes.

Optionally, the robot is used to determine (e.g., by experimentation) one or more of positions where pain is expected, degree (and other properties) of signals which prevent or mitigate pain, EMG or NMES signals which trigger pain and/or speeds or accelerations where pain is expected.

General

In an exemplary embodiment of the invention, the method of applying NMES is combined with the teachings of other applications filed by the applicant.

U.S. provisional application No. 60/633,442 filed on Dec. 7, 2004, filed as PCT application PCT/IL2005/000136 on Feb. 4, 2005, the disclosures of which are incorporated herein by reference, describe rehabilitation of balance. In an exemplary embodiment of the invention, NMES is used to help a patient coordinate two sides of a body, or to stimulate muscles in one part of the body relating to balance (e.g., a torso) when another part moves (e.g., legs).

U.S. provisional application No. 60/566,079 filed on Apr. 29, 2004, also filed as PCT application PCT/IL2005/000139 on Feb. 4, 2005, the disclosures of which are incorporated herein by reference, describe rehabilitation of fine motor control. In an exemplary embodiment of the invention, NMES is used to help a patient coordinate gross and fine motor motions (e.g., measuring a large muscle and stimulating a small muscle or vice versa) or to copy fine motor control from a healthy arm to a paretic arm.

U.S. provisional application No. 60/633,428 filed on Dec. 7, 2004, also filed as PCT application PCT/IL2005/000138 filed on Feb. 4, 2005, the disclosures of which are incorporated herein by reference, describe rehabilitation of gait. In an exemplary embodiment of the invention, NMES is used to coordinate the movement of two legs and/or of motion of different parts of a leg, for example, EMG measurements on a thigh (healthy or paretic) are used to drive NMES signals to a paretic calf.

U.S. provisional application No. 60/542,022 filed on Feb. 5, 2004, also filed as PCT applications PCT/IL2005/000140, PCT/IL2005/000141 and PCT/IL2005/000142 on Feb. 4, 2005, entitled "Methods and Apparatus for Rehabilitation and Training", the disclosures of which are incorporated herein by reference, describe rehabilitation devices of various types. In an exemplary embodiment of the invention, NMES stimulation and/or EMG measurement is provided in such devices.

U.S. provisional application No. 60/604,615 filed on Aug. 25, 2004, the disclosure of which is incorporated herein by reference, describes rehabilitation while measuring and/or otherwise taking into account brain plasticity. In an exemplary embodiment of the invention, NMES stimulation is provided in a manner which is coordinated with the activity of brain centers responsible for generating neural signal to the paretic limb and/or to receive signals from the paretic limb. Such a brain area may be detected, for example using EEG or fMRI methods.

U.S. provisional 60/666,136 filed on Mar. 29, 2005, the disclosure of which is incorporated herein by reference describes a system for retrofitting gymnastic equipment to be used for rehabilitation. Optionally, such retrofitting is used to make gymnastic equipment useful for setting electrode sequences as described herein, or for other uses instead of a robot/actuator.

U.S. provisional 60/665,886 filed on Mar. 28, 2005, the disclosure of which is incorporated herein by reference, describes a system for wellness, especially in the old age. Such wellness may include NMES stimulation to ensure usage of limbs and may include rehabilitation after stroke and assistance after injury, for example using the methods described herein.

As used herein, a "position" of an arm or another body part may include not just the spatial location of a particular portion of the arm or body part, but any other information needed to specify its spatial state, including, for example, how much it is bent at the elbow, how much the forearm is twisted, how much the wrist is bent, etc. In some embodiments, the velocity of the part and/or its orientation are controlled.

The invention has been described in the context of the best mode for carrying it out. It should be understood that not all features shown in the drawing or described in the associated text may be present in an actual device, in accordance with some embodiments of the invention. Various thresholds and values described herein may be varied, for example, personalized to match needs.

It will be appreciated that the above described methods of rehabilitation and muscle activation may be varied in many ways, including, omitting or adding steps, changing the order of steps and the types of devices used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are kits which include sets of a device, one or more tearing pins, one or more attachments and/or software. Also, within the scope is hardware, software and computer readable-media including such software which is used for carrying out and/or guiding the steps described herein, such as control of arm position and providing feedback. Section headings are provided for assistance in navigation and should not be considered as necessarily limiting the contents of the section. When used in the following claims, the terms "comprises", "includes", "have" and their conjugates mean "including but not limited to". It should also be noted that the device is suitable for both males and female, with male pronouns being used for convenience.

It will be appreciated by a person skilled in the art that the present invention is not limited by what has thus far been described. Rather, the scope of the present invention is limited only by the following claims.

The invention claimed is:

1. Apparatus for muscle activation, comprising:
at least one electrode adapted to deliver a neuromuscular stimulation (NMES) signal to a body portion of a patient;
at least one controller adapted to provide a NMES signal comprising a sequence of stimulation signals to said at least one electrode;
a mechanical motion element configured to be coupled to at least one of said body portion and a mirror body portion of the patient, wherein said mechanical motion element is operatively coupled to said at least one controller and wherein said at least one controller controls said NMES signal in conjunction with said mechanical motion element;
at least one EMG sensor coupled to said mirror body portion, wherein said controller is adapted to generate said NMES signal based on sensed EMG signals from said at least one EMG sensor; and,
at least one EMG sensor configured to be coupled to a minor body portion on a different person for measuring EMG signals from the different person, wherein said controller generates said NMES signal at least partly based on EMG signals received by the controller from the minor body portion of the different person.

2. Apparatus according to claim 1, wherein said mechanical motion element moves said body portion.

3. Apparatus according to claim 1, wherein said mechanical motion element measures motion of said body portion, which motion is in response to said NMES sequence.

4. Apparatus according to claim 1, wherein said mechanical motion element guides motion of said body portion, which motion is in response to said NMES signal.

5. Apparatus according to claim 1, wherein said mechanical motion element guides motion of said minor body portion, which NMES is generated in response to said motion.

6. Apparatus according to claim 1, comprising a programmer adapted to program NMES sequences for said electrodes.

7. Apparatus according to claim 6, wherein said programmer includes a sequence optimizer which modifies NMES sequences in response to at least one optimization criterion.

8. Apparatus according to claim 7, wherein said optimization criterion comprises the ability of a patient.

9. Apparatus according to claim 7, wherein said optimization criterion comprises electrode limitations.

10. Apparatus according to claim 7, wherein said optimization criterion comprises a quality of result, as measured by said mechanical motion element.

11. Apparatus according to claim 1, further comprising at least one EMG sensor coupled to said body portion for measuring EMG signals from the body portion.

12. Apparatus according to claim 11, wherein said controller generates a NMES signal responsive to at least one of an amplitude and existence of EMG signal at a location to which NMES is to be applied.

13. Apparatus according to claim 1, wherein said controller is adapted to generate an indication of which electrodes of said at least one electrode to use.

14. Apparatus according to claim 1, comprising a memory storing therein a plurality of NMES sequences, for at least one daily activity.

15. Apparatus according to claim 1, comprising a user input for generating a NMES sequence.

16. Apparatus according to claim 1, wherein said controller is adapted to generate a NMES sequence for use for said electrodes based on a desired motion of said body portion.

17. Apparatus according to claim 1, wherein said controller is adapted to modify a stored NMES sequence for use for said electrodes based on a desired motion of said body portion.

18. Apparatus according to claim 1, wherein said controller is adapted to compare an actual effect of a NMES sequence and a desired effect of said sequence and detect at least one deviation.

19. Apparatus according to claim 1, wherein said mechanical motion element is adapted to measure force applied by said body portion in response to said NMES.

20. Apparatus according to claim 1, comprising a calibrator adapted to calibrate at least one sensor associated with motion of said portion.

21. Apparatus according to claim 1, comprising an interactive user guide for electrode NMES programming.

22. Apparatus according to claim 1, wherein said electrodes are implantable.

23. Apparatus according to claim 1, wherein said electrodes form part of a prosthesis.

24. Apparatus according to claim 1, wherein said electrodes are adapted to be worn for a long term.

25. Apparatus according to claim 1, wherein said electrodes and at least one of said at least one controller are adapted to act independently of and removed from said mechanical motion element.

26. Apparatus according to claim 1, wherein said NMES sequence comprises a sequence for application to at least two muscles.

27. Apparatus according to claim 1, wherein said NMES sequence is at least 20 seconds long.

28. Apparatus according to claim 1, wherein said mechanical motion element comprises an actuator.

29. Apparatus according to claim 28, wherein said actuator comprises a robotic actuator with at least 3 degrees of motion.

30. A method of electrode setting for NMES, comprising:
measuring motion of a limb of a healthy person using at least one EMG sensor;
applying a NMES sequence to a limb of a paretic person which is the mirror of the limb of the healthy person;
measuring motion of the limb of the paretic person;
modifying said NMES sequence responsive to said measured motion of the healthy person and of the paretic person; and
repeating said applying, said measuring and said modifying, using a mechanical motion element to at least one of move said paretic person's limb, resist motion of said limb and measure motion of said limb until the measuring of the paretic person's limb matches the measuring of the healthy person's limb.

* * * * *